(12) United States Patent
Kojima et al.

(10) Patent No.: US 7,226,935 B2
(45) Date of Patent: Jun. 5, 2007

(54) HYPOGLYCEMIC AGENT

(75) Inventors: Yoshitane Kojima, Izumi (JP); Hiromu Sakurai, Nagaokakyo (JP); Yutaka Yoshikawa, Toyonaka (JP)

(73) Assignee: Japan Science and Technology Corporation, Saitama (JP)

( * ) Notice: Subject to any disclaimer, the term of this patent is extended or adjusted under 35 U.S.C. 154(b) by 419 days.

(21) Appl. No.: 10/470,786

(22) PCT Filed: Jan. 25, 2002

(86) PCT No.: PCT/JP02/00549

§ 371 (c)(1),
(2), (4) Date: Jul. 29, 2003

(87) PCT Pub. No.: WO02/060432

PCT Pub. Date: Aug. 8, 2002

(65) Prior Publication Data

US 2004/0077620 A1    Apr. 22, 2004

(30) Foreign Application Priority Data

Jan. 31, 2001 (JP) ............................. 2001-024532
Dec. 6, 2001 (JP) ............................. 2001-373289

(51) Int. Cl.
  *A61K 31/44* (2006.01)
  *C07D 211/70* (2006.01)
(52) U.S. Cl. ............... 514/334; 514/357; 546/329; 546/255; 546/257
(58) Field of Classification Search ................ 546/264, 546/329, 255, 257; 514/332, 357, 334
See application file for complete search history.

(56) References Cited

U.S. PATENT DOCUMENTS

| 5,948,388 A | 9/1999 | Steele et al. ............... 424/44 |
| 5,962,517 A | 10/1999 | Murad ..................... 514/474 |
| 2005/0130880 A1* | 6/2005 | Kojima et al. ............. 514/6 |

FOREIGN PATENT DOCUMENTS

| DE | 2013426 A1 | 10/1971 |
| DE | 2226267 A1 | 12/1973 |

(Continued)

OTHER PUBLICATIONS

Hcaplus 91:48687.*

(Continued)

*Primary Examiner*—Thomas McKenzie
*Assistant Examiner*—Binta Robinson
(74) *Attorney, Agent, or Firm*—Peter F. Corless; Christine C. O'Day; Edwards Angell Palmer & Dodge LLP

(57) ABSTRACT

A zinc(II) complex which is lowly toxic, has high insulin-like activity, and is effectively usable as a hypoglycemic agent for the prevention or treatment of diabetes; a hypoglycemic agent containing the complex; a medicinal preparation which contains the complex and is useful as a preventive/remedy for diabetes; and a food containing the complex, such as a health food or supplementary health food. The hypoglycemic agent contains an organic zinc(II) complex having as a ligand a compound selected among aminoalkylpyridines, bis-optically active amino acids, bisaminoalkylcarboxylic acids, oligopeptides, oligopseudopeptides, di-substituted aminocarboxylic acids, $\alpha$- and $\beta$-hydroxycarboxylic acids, vitamins, glutamine derivatives, etc.

2 Claims, 17 Drawing Sheets

| | FOREIGN PATENT DOCUMENTS | | |
|---|---|---|---|
| DE | 2457524 | A1 | 6/1976 |
| DE | 29701214 | U1 | 3/1997 |
| EP | 0 256 645 | | 2/1988 |
| EP | 0 658 568 | A1 | 6/1995 |
| EP | 0 755 917 | A1 | 1/1997 |
| JP | 53-38630 | | 4/1978 |
| JP | 54-55712 | | 5/1979 |
| JP | 61-282317 | | 12/1986 |
| JP | 6-1720 | | 1/1994 |
| WO | WO-79/00435 | | 7/1979 |
| WO | WO 87/01281 | | 3/1987 |
| WO | WO-87/01281 | | 3/1987 |
| WO | WO 87/04622 | | 8/1987 |
| WO | WO-99/07224 | | 2/1999 |
| WO | WO 01/39769 | A1 | 6/2001 |

OTHER PUBLICATIONS

Hcaplus 78:10.*
Hcaplus 128:18742.*
pubMed ID: 15301787.*
International Search Report.
I. Hwang et al., *Diabetes Obes Metab*, 5(5): pp. 317-324 Abstract Only t (2003).
M.J. Rosenthal et al., *Life Sciences*, vol. 70, pp. 337-348 (2001).
M.K. Song et al., *Metabolism*, vol. 47, No. 1, pp. 39-43 (1998).
M.K. Song et al., *Metabolism*, vol. 50, No. 1, pp. 53-59, (2001).
S.R. Narad et al., *Indian Journal of Experimental Biology*, vol. 34, pp. 81-82, (1996).
A. Abufarag et al., *Inorganic Chemistry*, 34(8):2207-2216 (1995).
H. Hemmerle et al., *Journal of Medicinal Chemistry*, 40(2):137-145 (1997).

* cited by examiner

HYPOGLYCEMIC AGENT

TECHNICAL FIELD

The present invention relates to a novel hypoglycemic agent which has insulin-like activity and is useful as a preventive/remedy for diabetes. Precisely, the invention relates to a novel hypoglycemic agent that contains a zinc(II) complex having a specific compound as a ligand and having insulin-like activity.

BACKGROUND ART

At present, treatment of type I (insulin-dependent) diabetes inevitably depends on subcutaneous insulin injection, and it is desired to develop an oral remedy for it in place of insulin. Some remedies have been developed for type II (insulin-independent) diabetes derived from stress, obesity, lack of exercise, ageing or the like, and have been tried in clinical treatment. However, none of them is a panacea and some often cause a problem of side effects. One of such remedies is vanadyl sulfate, and it has already been tried in clinical treatment in USA etc. In addition, vanadyl sulfate and bispicolinic acid/vanadyl complex are commercially available in USA as supplementary health foods.

On the other hand, it has been known that zinc(II) ion, which is known to be less toxic than vanadium, has insulin-like activity since around 1980 (L. Coulston and P. Dandona, "Insulin-like effects of $Zn^{2+}$ on adipocytes", *Diabetes*, 29, 665-7 (1980); J. M. May and C. S. Contoreggi, "The mechanism of the insulin-like effects of ionic zinc", *J. Biol. Chem.*, 257, 4362-8 (1982), and A. Shisheva, D. Gefel and Y. Shechter, "Insulin-like effects of zinc ion in vitro and in vivo" ($Zn^{2+}$ is the first agent other than vanadate that on oral administration is able to restore tissue ability to metabolism glucose), *Diabetes*, 41, 982-8 (1992)). Since vanadyl sulfate and zinc(II) ion (zinc sulfate and zinc chloride) are inorganic salts, they are hardly permeable through bio-membranes and are therefore hardly taken into living bodies. To overcome the problems, zinc(II) complexes, which are less toxic than vanadium and are favorably stable and fat-soluble and have insulin-like activity, may be more effective than vanadyl complexes, and developing them is desired.

On the other hand, zinc that is contained in brewer's yeast and seaweed extracts is commercially available in Japan as supplementary health foods.

Regarding zinc complexes, the present inventors have already filed a patent application that has been already published, International Publication WO01/39769A1 (international publication date: Jun. 7, 2001) "Hypoglycemic Agent Comprising Zinc(II) Organic Complex"; and some reports have been announced (for example, Y. Yoshikawa, E. Ueda, Y. Suzuki, N. Yanagihara, H. Sakurai and Y. Kojima, "New Insulinomimetic Zinc(II) Complexes of α-Amino Acids and their Dervatives with $Zn(N_2O_2)$ Coordination Mode", *Chem. Pharm. Bull.*, 49, 652-654 (2001); Yoshikawa, Ueda, Sakurai and Kojima, "Development and Study of Zinc(II) Complexes with Hypoglycemic Activity", *Biomed Res Trace Elements*, 12, 104-109 (2001)). However, it is desired to further develop more effective hypoglycemic agents comprising a complex that is less toxic and has higher activity and to develop foods such as health foods and supplementary health foods having the effect.

DISCLOSURE OF THE INVENTION

The present invention has been made in consideration of the above-mentioned current situation, and it aims to provide a zinc(II) complex that is less toxic, has high insulin-like activity and is effectively usable as a hypoglycemic agent for the prevention or treatment of diabetes, to provide a hypoglycemic agent that contains the said complex, to provide a medicinal preparation that contains the said complex and is useful as a preventive/remedy for diabetes, and to provide foods such as health foods and supplementary health food that contain the said complex.

The invention relates to a hypoglycemic agent that contains a zinc(II) organic complex having, as a ligand, any compound selected from the following (1) to (12):

(1) compounds of a general formula (1) (when they are optically-active compounds, they contain both (R)-form and (S)-form thereof):

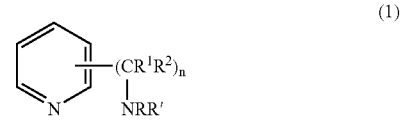

(wherein R, R', $R^1$ and $R^2$ each independently represents a hydrogen atom, an alkyl group, an aryl group, or an aralkyl group; n indicates an integer of from 1 to 3);

(2) compounds of a general formula (2):

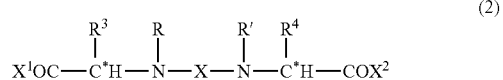

(wherein $X^1$ and $X^2$ each independently represents an alkoxy group, an amino group, a mono-lower alkylamino group, a di-lower alkylamino group, or a hydroxyl group; R and R' each independently represents a hydrogen atom, an alkyl group, an aryl group, or an aralkyl group; $R^3$ and $R^4$ each independently represents an alkyl group, a substituted alkyl group, or a heterocyclic group; R and $R^3$, and/or R' and $R^4$ may be taken together to form an alkylene group; C* represents an asymmetric carbon (either (R)-form or (S)-form); and X represents an alkylene group);

(3) compounds of a general formula (3):

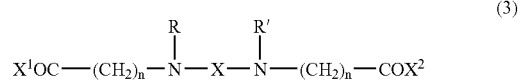

(wherein $X^1$ and $X^2$ each independently represents an alkoxy group, an amino group, a mono-lower alkylamino group, a di-lower alkylamino group, or a hydroxyl group; R and R' each independently represents a hydrogen atom, an alkyl group, an aryl group, or an aralkyl group; X represents an alkylene group; n indicates an integer of from 1 to 3);

(4) compounds of a general formula (4) (when they are optically-active compounds, they contain both (R)-form and (S)-form thereof):

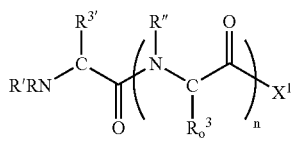
(4)

(wherein $X^1$ represents an alkoxy group, an amino group, a mono-lower alkylamino group, a di-lower alkylamino group, or a hydroxyl group; R, R' and R" each independently represents a hydrogen atom, an alkyl group, an aryl group, or an aralkyl group; $R^{3'}$ and $Ro^3$ each independently represents a hydrogen atom, an alkyl group, a substituted alkyl group, or a heterocyclic group; R and $R^{3'}$, and/or R" and $Ro^3$ may be taken together to form an alkylene group; n indicates an integer of from 1 to 3);

(5) compounds of a general formula (5) (when they are optically-active compounds, they contain both (R)-form and (S)-form thereof):

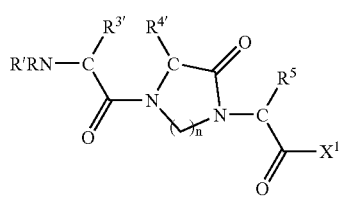
(5)

(wherein $X^1$ represents an alkoxy group, an amino group, a mono-lower alkylamino group, a di-lower alkylamino group, or a hydroxyl group; R and R' each independently represents a hydrogen atom, an alkyl group, an aryl group, or an aralkyl group; $R^{3'}$, $R^{4'}$ and $R^5$ each independently represents a hydrogen atom, an alkyl group, a substituted alkyl group, or a heterocyclic group; R and $R^{3'}$ may be taken together to form an alkylene group; n indicates an integer of from 1 to 3);

(6) compounds of a general formula (6) (when they are optically-active compounds, they contain both (R)-form and (S)-form thereof):

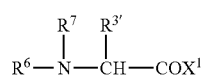
(6)

[wherein $X^1$ represents an alkoxy group, an amino group, a mono-lower alkylamino group, a di-lower alkylamino group, or a hydroxyl group; $R^{3'}$ represents a hydrogen atom, an alkyl group, a substituted alkyl group, or a heterocyclic group; $R^6$ and $R^7$ each independently represents an alkyl group, an aralkyl group, or a group of the following formula (6'):

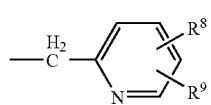
(6')

(wherein $R^8$ and $R^9$ each independently represents a hydrogen atom, an alkyl group, a nitro group, or a halogen atom); $R^6$ and $R^{3'}$ may be taken together to form an alkylene group];

(7) compounds of a general formula (7):

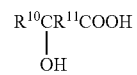
(7)

[wherein $R^{10}$ and $R^{11}$ each independently represents a hydrogen atom, an alkyl group, a hydroxyalkyl group, —$(CH_2)_m NRR'$, —$(CH_2)_m N^+RR'R''$, —$(CH_2)_m SR$, —$(CH_2)_m S^+RR'$, —$(CH_2)_m COOR$ or —$(CH_2)_m CONRR'$ (where m indicates an integer of from 0 to 4; and R, R' and R" each independently represents a hydrogen atom, an alkyl group, an aryl group, or an aralkyl group)];

(8) compounds of a general formula (8):

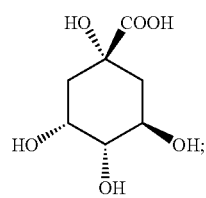
(8)

(9) compounds of a general formula (9):

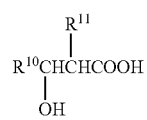
(9)

[wherein $R^{10}$ and $R^{11}$ each independently represents a hydrogen atom, an alkyl group, a hydroxyalkyl group, —$(CH_2)_m NRR'$, —$(CH_2)_m N^+RR'R''$, —$(CH_2)_m SR$, —$(CH_2)_m S^+RR'$, —$(CH_2)_m COOR$ or —$(CH_2)_m CONRR'$ (where m indicates an integer of from 0 to 4; and R, R' and R" each independently represents a hydrogen atom, an alkyl group, an aryl group, or an aralkyl group)];

(10) compounds of a general formula (10):

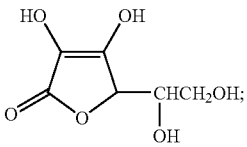
(10)

(11) compounds of a general formula (11):

$$\begin{array}{c} H_3C \\ \phantom{H_3C}\diagdown \\ \phantom{HHHH}S^+CH_2CH_2CHCOOH \cdot X_o^- \\ \phantom{H_3C}\diagup \phantom{HHHHHH} | \\ H_3C \phantom{HHHHHHHHH} NH_2 \end{array} \quad (11)$$

(wherein $X_o^-$ represents $Cl^-$, $Br^-$ or $I^-$);

(12) compounds of a general formula (12):

$$R^{12}NHCCH_2CHCHCOOH \quad (12)$$
$$\phantom{R^{12}NH}\|\phantom{CCH_2}|$$
$$\phantom{R^{12}NHC}O\phantom{CH_2}NHR^{13}$$

(wherein $R^{12}$ and $R^{13}$ each independently represents an alkyl group, an aryl group, or an aralkyl group).

The invention also relates to an oral formulation comprising the zinc(II) organic complex that contains, as a ligand, any compound selected from the above-mentioned general formulae (1) to (12).

Further, the invention relates to a pharmaceutical composition comprising, as an active ingredient, the zinc(II) organic complex that contains, as a ligand, any compound selected from the above-mentioned general formulae (1) to (12).

Still further, the invention relates to zinc(II) organic complexes having, as a ligand, a compound of the above-mentioned general formula (2), (3), (4), (5), (6), (9), (10), (11) or (12).

The invention also relates to a food that contains a zinc(II) organic complex having, as a ligand, any of L-lactic acid, quinic acid, L-carnitine (vitamin $B_T$), vitamin C, vitamin U or L-theanine.

BRIEF DESCRIPTION OF THE DRAWINGS

In FIG. 1, 1 indicates the result of a blank, 2 indicates the result of a control, 3 to 5 indicate the results of positive controls, and 6 to 20 indicate the results of the compounds of the invention.

In FIG. 2, 1 indicates the result of a blank, 2 indicates the result of a control, 3 to 5 indicate the results of positive controls, and 6 to 20 indicate the results of the compounds of the invention.

In FIG. 3, 1 indicates the result of a blank, 2 indicates the result of a control, 3 to 5 indicate the results of positive controls, and 21 to 38 indicate the results of the compounds of the invention.

BEST MODES OF CARRYING OUT THE INVENTION

Figure 1:
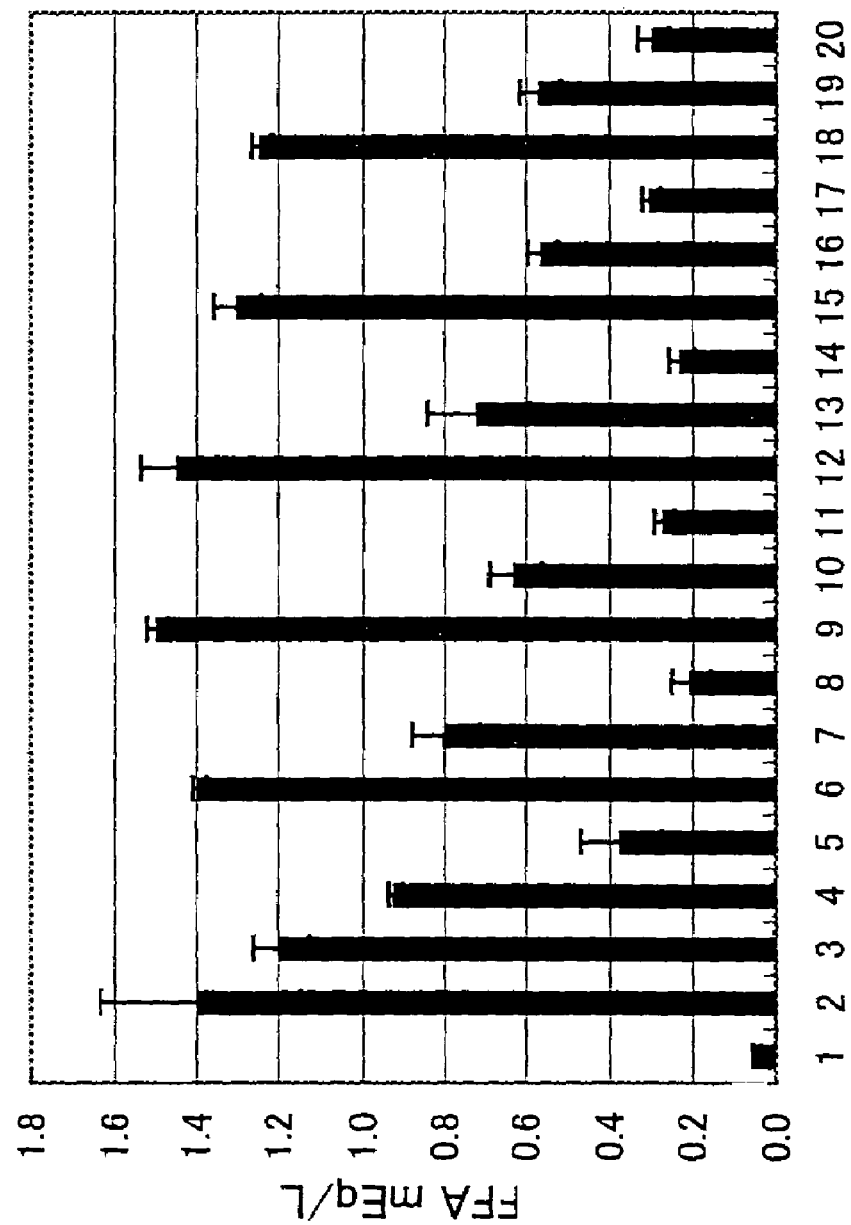
FIG. 1 shows the effect of zinc(II) organic complexes of the invention on release of fatty acids from fat cells.

The ligand for the zinc(II) organic complexes of the invention includes the compounds of the above-mentioned general formulae (1) to (12).

The compounds of formula (1) may be referred to, for example, as aminoalkylpyridines.

The compounds of formula (2) may be referred to, for example, as bis-optical active amino acids.

The compounds of formula (3) may be referred to, for example, as bisaminoalkylcarboxylic acids.

The compounds of formula (4) may be referred to, for example, as oligopeptides.

The compounds of formula (5) may be referred to, for example, as oligo-pseudopeptides.

The compounds of formula (6) may be referred to, for example, as di-substituted aminocarboxylic acids.

The compounds of formula (7) and those of formula (8) may be referred to, for example, as α-oxycarboxylic acids.

The compounds of formula (9) may be referred to, for example, as β-oxycarboxylic acids.

Of the compounds of formula (9), L-carnitine is vitamin B$_T$; the L-form compound of formula (10) is vitamin C; and the L-form compound of formula (11) is vitamin U.

R, R', R$^1$ and R$^2$ in formula (1), R and R' in formula (2), R and R' in formula (3), R, R' and R" in formula (4), and R and R' in formula (5) each independently represents a hydrogen atom, an alkyl group, an aryl group or an aralkyl group. For these, the alkyl group is, for example, a linear or branched lower alkyl group having from 1 to 6, preferably from 1 to 4 carbon atoms. More concretely, it includes, for example, a methyl group, an ethyl group, a propyl group, an isopropyl group, a butyl group, an isobutyl group, a secondary butyl group, and a tertiary butyl group. The aryl group includes, for example, a phenyl group, a tolyl group, a xylyl group, and a naphthyl group. The aralkyl group includes, for example, a benzyl group, a phenethyl group, a naphthylmethyl group, and a naphthylethyl group.

R$^3$ and R$^4$ in formula (2) each independently represents an alkyl group, a substituted alkyl group, or a heterocyclic group; and R$^{3'}$ and Ro$^3$ in formula (4), R$^{3'}$, R$^{4'}$ and R$^5$ in formula (5), and R$^{3'}$ in formula (6) each independently represents a hydrogen atom, an alkyl group, a substituted alkyl group, or a heterocyclic group. For these, the alkyl group is, for example, a linear or branched lower alkyl group having from 1 to 6, preferably from 1 to 4 carbon atoms. More concretely, for example, it is preferably a methyl group, an isopropyl group, an isobutyl group, or a secondary butyl group. The substituted alkyl group includes, for example, those derived from a lower alkyl group such as a methyl, ethyl or propyl group by substituting the hydrogen atom thereof with any of a hydroxyl group, a carboxyl group, an amino group, an amido group, a thiol group, a methylthio group, a phenyl group, a hydroxyphenyl group, or —NHC(NH$_2$)=NH. Concretely, for example, it includes —CH$_2$OH, —CH(CH$_3$)OH, —(CH$_2$)$_3$NHC(NH$_2$)=NH, —(CH$_2$)$_4$NH$_2$, —(CH$_2$)$_2$S(CH$_3$), —CH$_2$COOH, —CH$_2$CONH$_2$, —(CH$_2$)$_2$COOH, —(CH$_2$)$_2$CONH$_2$, —CH$_2$SH, a benzyl group, and a 4-hydroxyphenylmethyl group. The heterocyclic group is, for example, a saturated or unsaturated, monocyclic, polycyclic or condensed cyclic group having at least one of nitrogen, oxygen and sulfur atoms in the ring, of which one ring is 5- to 20-membered, preferably 5- to 10-membered, more preferably 5- to 7-membered and which may be condensed with a carbon cyclic group such as a cycloalkyl group, a cycloalkenyl group or an aryl group. Preferred examples of the group are an imidazolyl group and an indolyl group.

The alkylene group to be formed by R and R$^3$, R and R$^{3'}$, R' and R$^4$, R" and Ro$^3$, and R$^6$ and R$^{3'}$ includes, for example, an ethylene group, a propylene group, and a butylene group.

X$^1$ and X$^2$ in formula (2), X$^1$ and X$^2$ in formula (3), X$^1$ in formula (4), X$^1$ in formula (5), and X$^1$ in formula (6) each independently represents an alkoxy group, an amino group, a mono-lower alkylamino group, a di-lower alkylamino group, or a hydroxyl group. The alkoxy group for these is, for example, a linear or branched lower alkoxy group having from 1 to 6, preferably from 1 to 4 carbon atoms. More concretely, for example, it includes a methoxy group, an ethoxy group, a propoxy group, an isopropoxy group, a butoxy group, an isobutoxy group, a secondary butoxy group, and a tertiary butoxy group. The mono-lower alkylamino group is a substituted mono-lower alkylamino group with, for example, a linear or branched lower alkyl group having from 1 to 6, preferably from 1 to 4 carbon atoms. More concretely, for example, it includes a methylamino group, an ethylamino group, a propylamino group, an isopropylamino group, a butylamino group, and a tertiary butylamino group. The di-lower alkylamino group is a substituted di-lower alkylamino group with, for example, a linear or branched lower alkyl group having from 1 to 6, preferably from 1 to 4 carbon atoms. More concretely, for example, it includes a dimethylamino group, a diethylamino group, a dipropylamino group, a diisopropylamino group, a dibutylamino group, and a di-tertiary butylamino group.

R$^6$ and R$^7$ in formula (6) each independently represents an alkyl group, an aralkyl group, or a group of the following formula (6'):

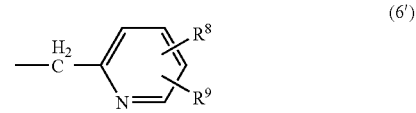

(6')

(wherein R$^8$ and R$^9$ each independently represents a hydrogen atom, an alkyl group, a nitro group, or a halogen atom). The alkyl group for these is, for example, a linear or branched lower alkyl group having from 1 to 6, preferably from 1 to 4 carbon atoms. More concretely, it includes, for example, a methyl group, an ethyl group, a propyl group, an isopropyl group, a butyl group, an isobutyl group, a secondary butyl group, and a tertiary butyl group. The aralkyl group includes, for example, a benzyl group, a phenethyl group, a naphthylmethyl group, and a naphthylethyl group. The halogen atom includes, for example, chlorine, bromine, iodine and fluorine atoms.

X in formulae (2) and (3) represents an alkylene group. The alkylene group is, for example, a lower alkylene group having from 1 to 6, preferably from 1 to 4 carbon atoms. More concretely, for example, it includes an ethylene group, a trimethylene group, a methylethylene group, a propylene group, a tetramethylene group, and a 1,2-dimethylethylene group.

R$^{10}$ and R$^{11}$ in formulae (7) and (9) each independently represents a hydrogen atom, an alkyl group, a hydroxyalkyl group, —(CH$_2$)$_m$NRR', —(CH$_2$)$_m$N$^+$RR'R", —(CH$_2$)$_m$SR, —$(CH_2)_m S^+ RR'$, —$(CH_2)_m COOR$ or —$(CH_2)_m CONRR'$ (where m indicates an integer of from 0 to 4; and R, R' and R" each independently represents a hydrogen atom, an alkyl group, an aryl group, or an aralkyl group). For these, the alkyl group is, for example, a linear or branched lower alkyl group having from 1 to 6, preferably from 1 to 4 carbon atoms. More concretely, it includes, for example, a methyl group, an ethyl group, a propyl group, an isopropyl group, a butyl group, an isobutyl group, a secondary butyl group, and a tertiary butyl group. The hydroxyalkyl group is, for example, the above-mentioned alkyl group of which one hydrogen atom is substituted with a hydroxyl group. More concretely, for example, it includes a hydroxymethyl group, an α-hydroxyethyl group, a β-hydroxyethyl group, a hydroxypropyl group, and a hydroxybutyl group. In the other groups, R, R' and R" each independently represents a hydrogen atom, an alkyl group, an aryl group, or an aralkyl group. For the alkyl group, the aryl group and the aralkyl group, referred to are the same mentioned hereinabove for R, R', $R^1$ and $R^2$ in formula (1).

$R^{12}$ and $R^{13}$ in formula (12) each independently represents an alkyl group, an aryl group or an aralkyl group. For the alkyl group, the aryl group and the aralkyl group, referred to are the same mentioned hereinabove for R, R', $R^1$ and $R^2$ in formula (1).

The zinc(II) organic complexes of the invention may be produced by known methods (for example, as in U.S. Pat. No. 5,219,847) or according to such known methods. For example, a solution of a zinc salt is added to a solution of the intended ligand to form a zinc(II) organic complex, and which is then isolated. For the solvent, water is generally preferred, but an organic solvent or a mixed solvent may also be used. The zinc salt solution is preferably an aqueous solution of an inorganic zinc such as zinc sulfate, zinc nitrate or zinc chloride. Preferably, the pH of the reaction solution is controlled, if desired. For the pH-regulating agent, usable is an aqueous basic solution of, for example, sodium hydroxide, lithium hydroxide, potassium hydroxide or barium hydroxide.

More concretely, referred to are Examples described hereinunder.

Of the zinc(II) organic complexes of the invention, those having, as a ligand, a compound of formula (2), (3), (4), (5), (6), (9), (10), (11) or (12) are all novel compounds.

As is obvious from Test Examples to be described hereinunder, the zinc(II) organic complexes of the invention have insulin-like activity or hypoglycemic activity, and are useful as preventives/remedies for diabetes and hypertension.

Accordingly, the invention provides a pharmaceutical composition that comprises the above-mentioned zinc(II) organic complex of the invention and a pharmaceutically-acceptable carrier.

The pharmaceutical composition may be in the form of a medicinal preparation that comprises the zinc(II) organic complex of the invention serving as an active ingredient, along with a pharmaceutically-acceptable carrier such as an organic or inorganic, solid or liquid vehicle suitable for oral administration, parenteral administration or local administration. The medicinal preparation may be in any form of capsules, tablets, pills, granules, powders, inhalants, suppositories, solutions, lotions, suspensions, emulsions, ointments and gels. If desired, the preparation may contain an auxiliary aid, a stabilizer, a wetting agent, a emulsifier, a buffer and any other ordinary additives.

The invention provides an oral formulation that contains the zinc(II) organic complex. The oral formulation of the invention contains the zinc(II) organic complex having insulin-like activity or hypoglycemic activity. Accordingly, the invention provides an oral remedy/preventive for diabetes. The invention also provides use of the zinc(II) organic complex for producing such an oral preventive/remedy for diabetes, and provides a method for preventing and treating diabetes by orally administering an effective dose of the oral preventive/remedy for diabetes.

The effective dose of the zinc(II) organic complex of the invention for prevention/treatment of the disease varies depending on the age and the condition of the cases to which it is administered. In general, however, a mean dose of the zinc(II) organic complex of the invention may fall between about 0.1 mg/patient and about 1000 mg/patient, and it may be administered once or a few times a day.

Figure 2:
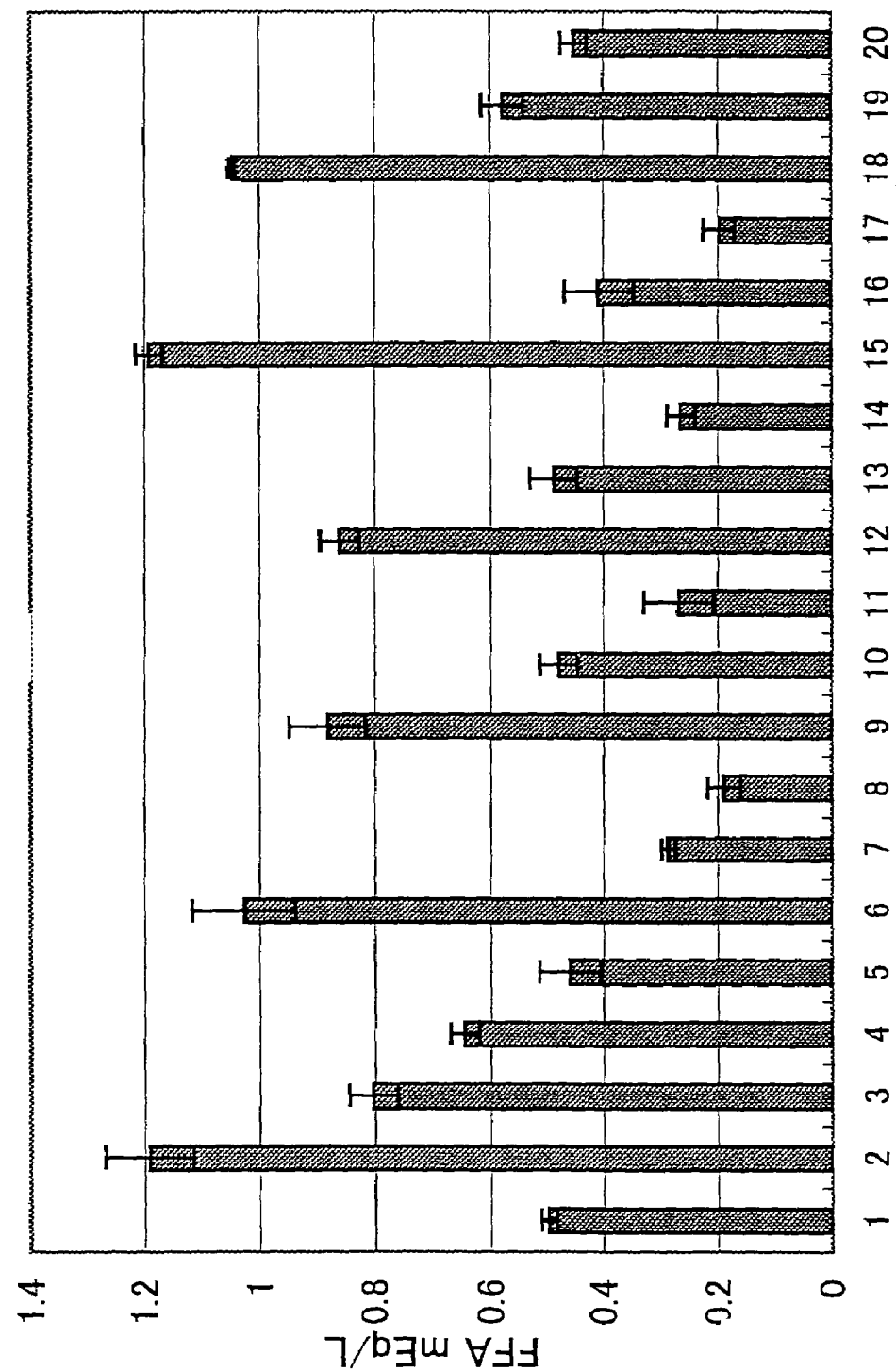
FIG. 2 shows the effect of zinc(II) organic complexes of the invention on release of fatty acids from fat cells.
Figure 3:
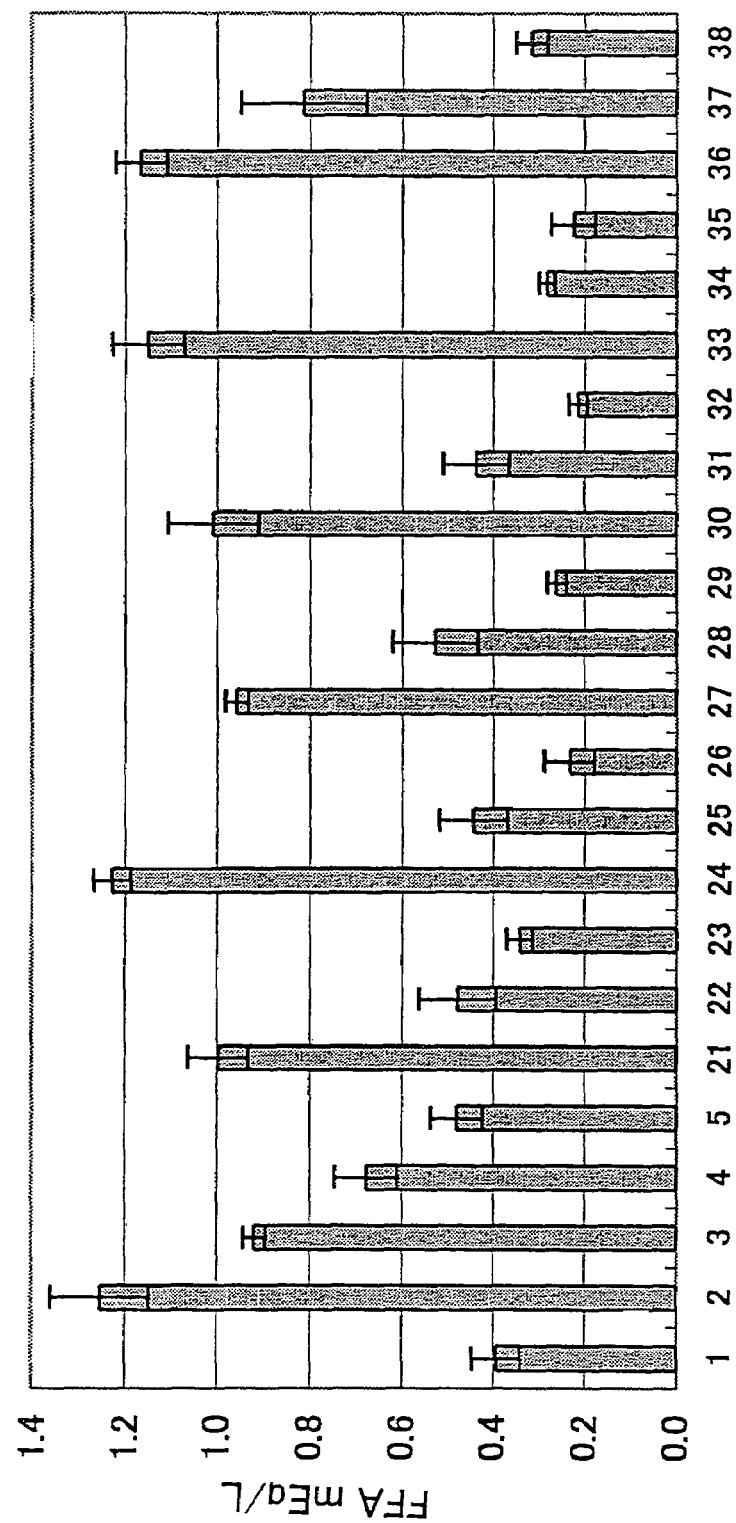
FIG. 3 shows the effect of zinc(II) organic complexes of the invention on release of fatty acids from fat cells.

FIG. 1, FIG. 2 and FIG. 3 show test results that indicate the capability of the zinc(II) organic complex of the invention to inhibit the release of fatty acids from the fat cells in rats.

FIG. 1, FIG. 2 and FIG. 3 each shows the free fatty acid inhibiting effect of the zinc(II) organic complex of the invention added to epinephrine-stimulated rat fat cells.

In FIG. 1, 1 indicates a blank, 2 indicates a control, 3 to 5 indicate positive controls with oxovanadium sulfate ($VOSO_4$), and 6 to 20 indicate the compounds of the invention.

6 to 8 are with N,N'-ethylene-bis-β-alanine/zinc(II) complex [$Zn(\beta AeA\beta)(H_2O)_2$]; 9 to 11 are with N,N'-trimethylene-bis-L-valine/zinc(II) complex [$Zn(VtV)(H_2O)_2$]; 12 to 14 are with N,N-dipyridylmethyl-L-valine/zinc(II) complex [$Zn(^{pm2}V)(ClO_4)$]; 15 to 17 are with N,N-dipyridylmethyl-D-valine/zinc(II) complex [$Zn(^{pm2}V_R)(ClO_4)$]; 18 to 20 are with N-6-methylpyridylmethyl-L-aspartic acid/zinc(II) complex [$Zn(^{6Me-pm}D)$].

The concentration of the compound used is $10^{-4}$ M, $5 \times 10^{-4}$ M, and $10^{-3}$ M, respectively.

In FIG. 2, 1 indicates a blank, 2 indicates a control, 3 to 5 indicate positive controls with oxovanadium sulfate ($VOSO_4$), and 6 to 20 indicate the compounds of the invention.

6 to 8 are with bis(2-aminomethylpyridine)/zinc(II) complex [$Zn(2\text{-}AM\text{-}py)_2(H_2O)Cl_2$]; 9 to 11 are with bis-(R)-2-(1-aminoethyl)pyridine (=α-pyridylethylamine)/zinc(II) complex [$Zn((R)\text{-}2\text{-}(1\text{-}AE)\text{-}py)_2(H_2O)Cl_2$]; 12 to 14 are with bis-(S)-2-(1-aminoethyl)pyridine/zinc(II) complex [Zn((S)-2-(1-AE)-py)$_2$(H$_2$O)Cl$_2$]; 15 to 17 are with L-aspartyl-L-phenylalanine methyl ester (aspartame)/zinc(II) complex [$Zn(AspF\text{—}OMe)(H_2O)_2$]; 18 to 20 are with bis(glycyl-N,N'-ethylene-L-alanyl-L-alanine ethyl ester)/zinc(II) complex [$Zn(Gly\text{-}eAA\text{-}OEt)_2Cl_2$].

The concentration of the compound used is $10^{-4}$ M, $5 \times 10^{-4}$ M, and $10^{-3}$ M, respectively.

Further, in FIG. 3, 1 indicates a blank, 2 indicates a control, 3 to 5 indicate positive controls with oxovanadium sulfate ($VOSO_4$), and 21 to 38 indicate the compounds of the invention.

21 to 23 are with bis(L-lactic acid)/zinc(II) complex [$Zn(Lac)_2$]; 24 to 26 are with bis(quinic acid)/zinc(II) complex [$Zn(Qui)_2$]; 27 to 29 are with bis(L-carnitine)/zinc(II) complex [$Zn(Car)_2Cl_2$]; 30 to 32 are with bis(L-ascorbic acid)/zinc(II) complex [$Zn(Vit\text{-}C)_2$]; 33 to 35 are with bis(vitamin U)/zinc(II) complex [$Zn(Vit\text{-}U)Cl_2$]; and 36 to 38 are with bis(L-theanine)/zinc(II) complex [$Zn(Tea)_2$].

The concentration of the compound used is $10^{-4}$ M, $5 \times 10^{-4}$ M, and $10^{-3}$ M, respectively.

The "blank" 1 in FIG. 1, FIG. 2 and FIG. 3 shows the value of free fatty acids (FFA) in spontaneous release from cells; and the "control" 2 therein shows the value thereof released through epinephrine stimulation. 3 to 5 with oxovanadium sulfate "VOSO$_4$" in FIG. 1, FIG. 2 and FIG. 3 are comparative examples.

Table 1 below shows IC$_{50}$ (mM), the concentration of the test compound, zinc(II) complex of the invention that inhibits 50% fatty acid release calculated based on the results of the tests. In Table 1, IC$_{50}$ (mM) of "VOSO$_4$" is 1.00 mM, and the value of the other compounds is a relative value to it.

TABLE 1

| Complex | IC$_{50}$ (mM) |
|---|---|
| Zn(2-AM-py)$_2$Cl$_2$ | 0.85 |
| Zn((R)-2-AM-py)$_2$Cl$_2$ | 0.40 |
| Zn((S)-2-AM-py)$_2$Cl$_2$ | 0.39 |
| Zn(βAeAβ) | 0.82 |
| Zn(VtV) | 0.92 |
| Zn(AspF-OMe)$_2$ | 1.11 |
| Zn(Gly-eAA-OEt)$_2$Cl$_2$ | 0.85 |
| Zn($^{pm2}$V)ClO$_4$ | 0.79 |
| Zn($^{pm2}$V$_R$)ClO$_4$ | 0.92 |
| Zn($^{6Me-pm}$D) | 0.86 |
| Zn(Lac)$_2$ | 0.81 |
| Zn(Qui)$_2$ | 0.98 |
| Zn(Car)$_2$Cl$_2$ | 0.80 |
| Zn(Vit-C)$_2$ | 0.80 |
| Zn(Vit-U)Cl$_2$ | 0.84 |
| Zn(Tea)$_2$ | 1.23 |
| VOSO$_4$ | 1.00 |

The data confirms that, as compared with VOSO$_4$, the zinc(II) organic complex of the invention significantly inhibits fatty acids from being released from rat fat cells, indicating that the complex is favorable for preventives/remedies for diabetes and hypertension.

In addition, the zinc(II) organic complex of the invention is usable in foods such as health foods, supplementary health foods, nutrient foods and supplementary nutrient foods that have hypoglycemic activity.

In particular, the zinc(II) organic complex of the invention that has a natural ligand such as L-lactic acid, quinic acid, L-carnitine (vitamin B$_T$), vitamin C, vitamin U or L-theanine is especially favorable for foods such as health foods, supplementary health foods, nutrient foods and supplementary nutrient foods that have hypoglycemic activity.

The foods of the invention may contain any other foods, food additives, vitamins and/or minerals.

These other foods, food additives, vitamins and minerals may be any ones that are generally used and may be used in future in the field of medicines and foods. Naturally, however, since the foods of the invention are health foods, supplementary health foods, nutrient foods, supplementary nutrient foods and the like that have hypoglycemic activity, the additional foods, food additives, vitamins and minerals to be added thereto must not interfere with the effect of the foods of the invention.

Regarding the shape thereof, the foods of the invention may be in any form of powders, granules, tablets, capsules, liquids, gels and any others.

Not limited to those having the shape as above, foods and drinks that are produced by adding the zinc(II) organic complex of the invention to already-existing foods (foods and drinks) are all within the scope of the foods of the invention.

Examples of the foods and drinks are drinks such as refreshing drinks, nutrient drinks, fruit drinks, lactic acid drinks (including concentrated stocks and/or controlled powders to give these drinks); frozen confectionery such as ice creams, sherbets; processed cereals such as buckwheat noodles, wheat noodles, baked goods, rice cakes, dough for jiaozi (Chinese dumpling with minced pork and vegetable stuffing); confectionery such as caramels, candies, chocolates, snacks, biscuits, cookies, crackers, jellies, jams; processed marine and stock farm products such as steamed fish pastes, pounded fish cakes, hams, sausages; milk products such as processed milks, cheeses, butters; oils and fats, and processed oils and fats such as margarines, lards, mayonnaises; seasonings such as soy sauces, sauces, soybean pastes, juices pressed from bitter oranges, tangleweed extracts, soup stocks; various everyday dishes; pickles; and other various types of supplementary nutrient and health foods. Needless-to-say, these are not limitative.

The foods of the invention, which comprise an organic compound capable of forming a complex with zinc and a zinc source, are much expected for health (supplementary) foods, more concretely, for example, supplements (specific health foods, so-called "tokuho") that normalize the blood glucose level of diabetics and others and are effective for prevention and treatment of glucose tolerance disorders, diabetes (e.g., type II diabetes), insulin-resistant syndromes (e.g., insulin receptor disorders), polycystic ovary syndromes, hyperlipemia, atherosclerosis, cardiovascular disorders (e.g., stenocardia, cardiac insufficiency), hyperglycemia, hypertension, stenocardia, pulmonary hypertension, congestive cardiac insufficiency, diabetic complications (e.g., diabetic gangrene, diabetic arthropathy, diabetic glomerulosclerosis, diabetic skin disorders, diabetic neuropathy, diabetic cataract, diabetic retinopathy), skin disorders, taste disorders, etc.

In addition, the foods of the invention are much expected for nutrient (supplementary) foods having the ability of insulin activation and blood glucose level normalization.

EXAMPLES

The invention is described in more detail with reference to the following Examples and Test Examples, which, however, are not intended to restrict the scope of the invention.

Example 1

Production of bis(2-aminomethylpyridine)/zinc(II) complex [Zn(2-AM-py)$_2$(H$_2$O)Cl$_2$]

An ethanol solution of zinc(II) chloride (5 mmols) was dropwise added to an ethanol solution of 2-aminomethylpyridine (10 mmols) with stirring. After this was left overnight, the resulting precipitate was taken out through filtration, washed with ethanol and ether, and dried to obtain a white product as entitled.

Yield: 30%. m.p.: 197-199° C.
Molecular formula: Zn(C$_6$H$_8$N$_2$)$_2$Cl$_2$.0.9H$_2$O,
Molecular weight: 368.8.
Elementary analysis:

| cald. (%) | C; 39.08, | H; 4.86, | N; 15.19 |
| found (%) | C; 39.07, | H; 4.49, | N; 15.20, |

Figure 4:
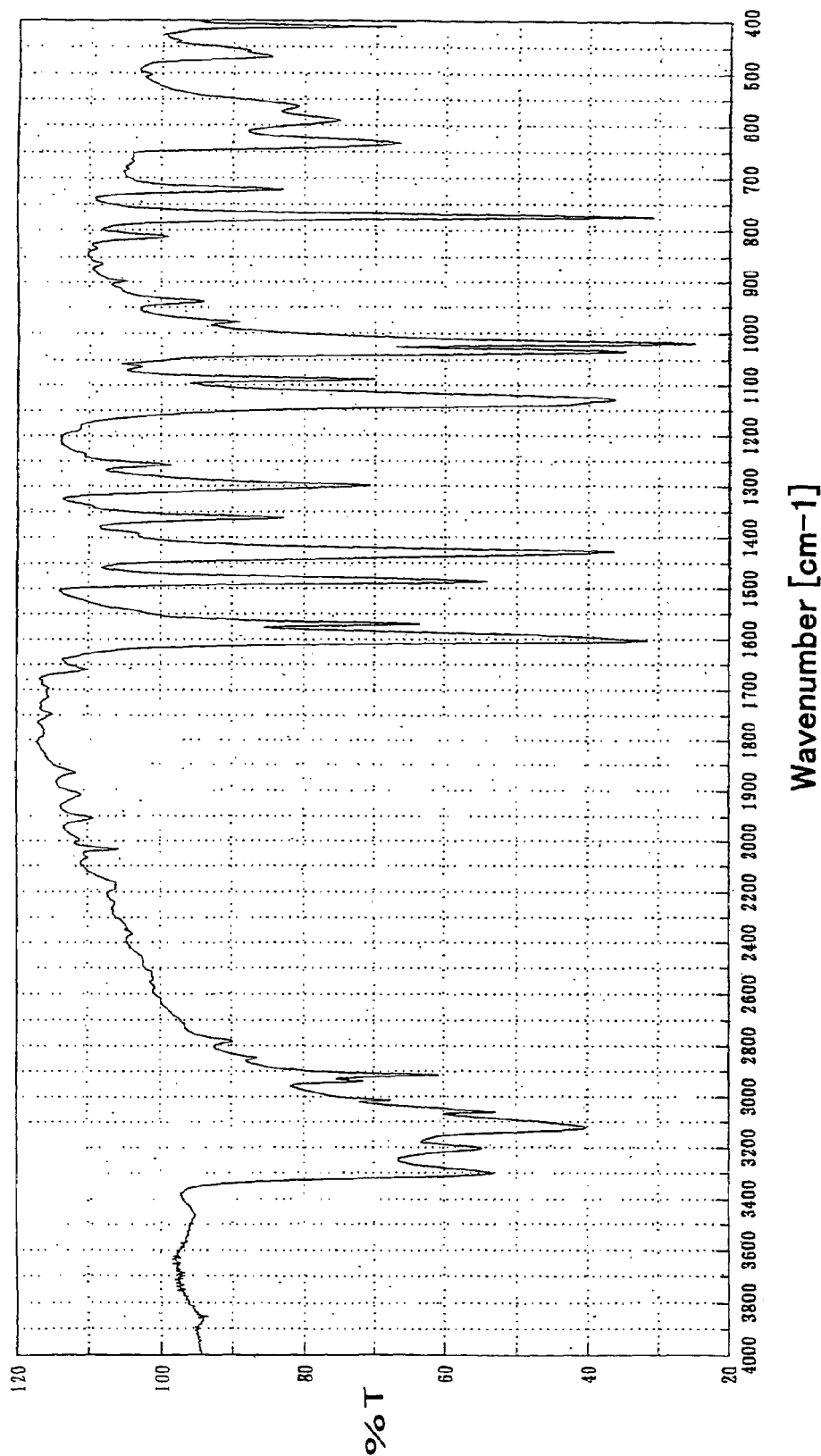
FIG. 4 shows a full chart of the IR absorption spectrum (IR) of bis(2-aminomethylpyridine)/zinc(II) complex [Zn(2-AM-py)$_2$(H$_2$O)Cl$_2$] of the invention.

IR (KBr): full chart in FIG. 4.

In the same manner as above, produced were bis-(R)- and (S)-2-(1-aminoethyl)pyridine (=α-pyridylethylamine/zinc (II) complex [Zn((R)-2-(1-AE)-py)$_2$(H$_2$O)Cl$_2$ and Zn((S)-2-

(1-AE)-py)$_2$(H$_2$O)Cl$_2$]. Bis-(R)- and (S)-2-(1-aminoethyl)pyridine was produced according to a reference (Uenishi et al. *Heterocycles*, 52, 719 (2000)).

R-Form
  Yield: 64%. m.p.: 163-165° C. [α]$_D$: +1.2°.
  Molecular formula: Zn(C$_7$H$_{10}$N$_2$)$_2$Cl$_2$.0.2H$_2$O,
  Molecular weight: 384.2.
  Elementary analysis:

| cald. (%) | C; 43.76, | H; 5.34, | N; 14.54 |
| found (%) | C; 43.92, | H; 5.34, | N; 14.54. |

S-Form
  Yield: 77%. m.p.: 162-164° C. [α]$_D$: −1.2°.
  Molecular formula: Zn(C$_7$H$_{10}$N$_2$)$_2$Cl$_2$.0.5H$_2$O,
  Molecular weight: 389.6.
  Elementary analysis:

| cald. (%) | C; 43.16, | H; 5.43, | N; 14.38 |
| found (%) | C; 43.22, | H; 5.36, | N; 14.43. |

Example 2

Production of N,N'-ethylene-bis-β-alanine/zinc(II) complex [Zn(βAeAβ)(H$_2$O)$_2$]

N,N'-ethylene-bis-β-alanine (10 mmols) was dissolved in an aqueous solution of barium hydroxide (5 mmols). To the resulting solution, dropwise added was an aqueous solution of zinc(II) sulfate (5 mmols) with stirring. After left for 1 day, the resulting precipitate was separated through filtration, and the filtrate was concentrated. The resulting white precipitate was recrystallized from hot water to obtain a white product as entitled.
  Yield: 92%.
  IR (KBr): ν C=O; 1568 cm$^{-1}$.
  Molecular formula: Zn(C$_8$H$_{14}$N$_2$O$_4$)(H$_2$O)$_2$,
  Molecular weight: 306.2.
  Elementary analysis:

| cald. (%) | C; 29.58, | H; 5.46, | N; 9.86 |
| found (%) | C; 29.33, | H; 5.39, | N; 9.76. |

Example 3

Production of N,N'-trimethylene-bis-L-valine/zinc(II) complex [Zn(VtV)(H$_2$O)$_2$]

N,N'-ethylene-bis-L-valine (5 mmols) was dissolved in an aqueous solution of barium hydroxide (10 mmols). To the resulting solution, dropwise added was an aqueous solution of zinc(II) sulfate (5 mmols) with stirring. After left for 1 day, the resulting precipitate was separated through filtration, and the filtrate was concentrated. The resulting white precipitate was recrystallized from hot water to obtain a white product as entitled.
  Yield: 79%.
  IR (KBr): ν C=O; 1591 cm$^{-1}$. S-form: [α]$_D$: +23.3°.

Molecular formula: Zn(C$_{13}$H$_{24}$N$_2$O$_4$)(H$_2$O)$_2$,
Molecular weight: 397.2.
Elementary analysis:

| cald. (%) | C; 39.31, | H; 7.97, | N; 7.05 |
| found (%) | C; 39.21, | H; 7.53, | N; 7.03. |

Example 4

Production of L-aspartyl-L-phenylalanine methyl ester (aspartame)/zinc(II) complex [Zn(AspF—OMe)(H$_2$O)$_2$]

Ba(OH)$_2$/8H$_2$O (5 mmols) was added to an aqueous solution of aspartame (10 mmols). To the resulting solution, dropwise added was an aqueous solution of zinc(II) sulfate (5 mmols) with stirring. After left for 1 day, the resulting precipitate was separated through filtration, and the filtrate was concentrated. This was dried in vacuum to obtain a white product as entitled.
  Yield: 62%. S-form: [α]$_D$: +11.6°.
  IR (KBr): ν C=O (amido); 1655 cm$^{-1}$, ν C=O (ester); 1742 cm$^{-1}$.
  Molecular formula: Zn(C$_{13}$H$_{24}$N$_2$O$_4$)(H$_2$O)$_2$,
  Molecular weight: 695.2.
  Elementary analysis:

| cald. (%) | C; 48.37, | H; 5.63, | N; 8.06 |
| found (%) | C; 48.38, | H; 5.48, | N; 8.19. |

Example 5

Production of bis(glycyl-N,N'-ethylene-L-alanyl-L-alanine ethyl ester)/zinc(II) complex [Zn(Gly-eAA-OEt)$_2$Cl$_2$]

Barium hydroxide (5.5 mmols) dissolved in a small quantity of water was added to a water/methanol (1:1) solution with glycyl-N,N'-ethylene-L-alanyl-L-alanine ethyl ester monohydrochloride (11 mmols) dissolved therein. To the resulting solution, dropwise added was an aqueous solution of zinc(II) sulfate (5 mmols) with stirring. After left for 1 day, the resulting precipitate was separated through filtration, and the filtrate was concentrated. This was dried to obtain a white product as entitled.
  Yield: 82%. m.p.: 102-110° C. [α]$_D$: +59.8°.
  IR (KBr): ν C=O (amido); 1638 cm$^{-1}$, ν C=O (ester); 1734 cm$^{-1}$.
  Molecular formula: Zn(C$_{12}$H$_{21}$N$_3$O$_4$)$_2$Cl$_2$.4H$_2$O,
  Molecular weight: 751.0.
  Elementary analysis:

| cald. (%) | C; 38.38, | H; 6.71, | N; 11.19 |
| found (%) | C; 37.92, | H; 6.64, | N; 11.56. |

Glycyl-N,N'-ethylene-L-alanyl-L-alanine ethyl ester monohydrochloride (Gly-eAA-OEt/HCl) used herein was prepared by producing Boc-Gly-eAA-OEt according to a reference, T. Yamashita, Y. Kojima, K. Hirotsu, A. Ohsuka, *Int. J. Peptide Protein Res.*, 33, 110 (1989), and deprotecting it with 4 N HCl/AcOEt.

Example 6

Production of N,N-dipyridylmethyl-L-valine/zinc (II) complex [Zn($^{pm2}$V)(ClO$_4$)]

Barium hydroxide (5 mmols) dissolved in a small quantity of water was added to a water/methanol (1:1) solution with N,N-dipyridylmethyl-L-valine methyl ester monohydrochloride (10 mmols) dissolved therein. To the resulting solution, dropwise added was an aqueous solution of zinc(II) sulfate (10 mmols) with stirring. After this was left for 1 hour, barium perchlorate (5 mmols) was added thereto and stirred overnight. The resulting precipitate was separated through filtration, and the filtrate was concentrated. This was dried to obtain a white product as entitled.

Yield: 87%. m.p.: 208-220° C. [α]$_D$: −101.0°.
IR (KBr): ν C=O (amido); 1638 cm$^{-1}$, ν C=O (ester); 1734 cm$^{-1}$.
Molecular formula: Zn(C$_{17}$H$_{20}$N$_3$O$_6$)ClO$_4$.1.8H$_2$O,
Molecular weight: 524.5.
Elementary analysis:

| cald. (%) | C; 38.38, | H; 6.71, | N; 11.19 |
|---|---|---|---|
| found (%) | C; 37.92, | H; 6.64, | N; 11.56. |

In the same manner as above, produced were zinc(II) complexes with N,N-dipyridylmethyl-D-valine and N-6-methylpyridylmethyl-L-aspartic acid [Zn($^{pm2}$V$_R$)(ClO$_4$) and Zn($^{6Me-pm}$D)].

N,N-dipyridylmethyl-D-valine/zinc(II) complex
Yield: 42%. m.p.: 210-218° C. [α]$_D$: +107.4°.
IR (KBr): ν C=O (amido); 1638 cm$^{-1}$, ν C=O (ester); 1734 cm$^{-1}$.
Molecular formula: Zn(C$_{17}$H$_{20}$N$_3$O$_6$)Cl$_2$.1.8H$_2$O,
Molecular weight: 495.6.
Elementary analysis:

| cald. (%) | C; 41.20, | H; 4.80, | N; 8.48 |
|---|---|---|---|
| found (%) | C; 40.94, | H; 4.21, | N; 8.38. |

N-6-methylpyridylmethyl-L-aspartic acid/zinc(II) complex
Yield: 82%. m.p.: 279-283° C.
IR (KBr): ν C=O; 1590 cm$^{-1}$.
Molecular formula: Zn(C$_{11}$H$_{10}$N$_2$O$_4$).2.7H$_2$O,
Molecular weight: 348.2.
Elementary analysis:

| cald. (%) | C; 37.94, H; 4.46, N; 8.04 |
|---|---|
| found (%) | C; 38.02, H; 4.70, N; 8.07. |

Ester, hydrochloride with N,N-dipyridylmethyl-L-valine, N,N-dipyridylmethyl-D-valine and N-6-methylpyridylmethyl-L-aspartic acid hydrochloride used herein were prepared and saponified according to the method described in a reference, K. Yamato et al., *Chem. Lett.*, 1999, 295.

Example 7

Production of L-lactic Acid (Lac)/zinc(II) complex [Zn(Lac)$_2$]

An aqueous solution of zinc sulfate (5 mmols) was dropwise added to an aqueous solution of lactic acid (10 mmols) and lithium hydroxide (10 mmols). This was kept stirred overnight, and the resulting precipitate was taken out through filtration and washed with water to obtain the intended product.

Yield: 90%. m.p.: >300° C. [α]$_D$: −11.1° (CH$_3$OH).
Molecular formula: Zn(C$_6$H$_{30}$O$_6$).2H$_2$O,
Molecular weight: 279.6.
Elementary analysis:

| cald. (%) | C; 25.78, H; 5.05 |
|---|---|
| found (%) | C; 25.87, H; 5.05. |

Example 8

Production of bis(quinic acid)/zinc(II) complex [Zn(Qui)$_2$]

An aqueous solution of zinc(II) sulfate (2.5 mmols) was added to an aqueous solution of quinic acid (5 mmols) and barium (2.5 mmols). The resulting precipitate was separated through filtration, the filtrate was concentrated, and the resulting residue was reprecipitated from water/methanol to obtain the intended product.

Yield: 49%. m.p.: >300° C. [α]$_D$: +207° (H$_2$O).
Molecular formula: Zn(C$_{14}$H$_{22}$O$_{12}$)/0.2H$_2$O,
Molecular weight: 451.3.
Elementary analysis:

| cald. (%) | C; 37.26, H; 5.00 |
|---|---|
| found (%) | C; 37.24, H; 4.84. |

Example 9

Production of L-carnitine (γ-trimethyl-β-hydroxybutyrobetaine=Car)/zinc(II) complex [Zn(Car)$_2$Cl$_2$]

An aqueous solution of zinc(II) chloride (5 mmols) was dropwise added to an aqueous solution of L-carnitine (10 mmols) with stirring. After stirred for 2 hours, the reaction liquid was concentrated, and the residue was processed with ethanol to obtain the intended product, powdery crystal.

Yield: 88%. m.p.: 173-175° C. [α]$_D$: +3.2° (H$_2$O).
Molecular formula: Zn(C$_{14}$H$_{30}$N$_2$O$_6$)Cl$_2$/H$_2$O,
Molecular weight: 476.7.
Elementary analysis:

| cald. (%) | C; 35.27, H; 6.77, N; 5.88 |
|---|---|
| found (%) | C; 35.04, H; 6.82, N; 5.67, |

Figure 5:
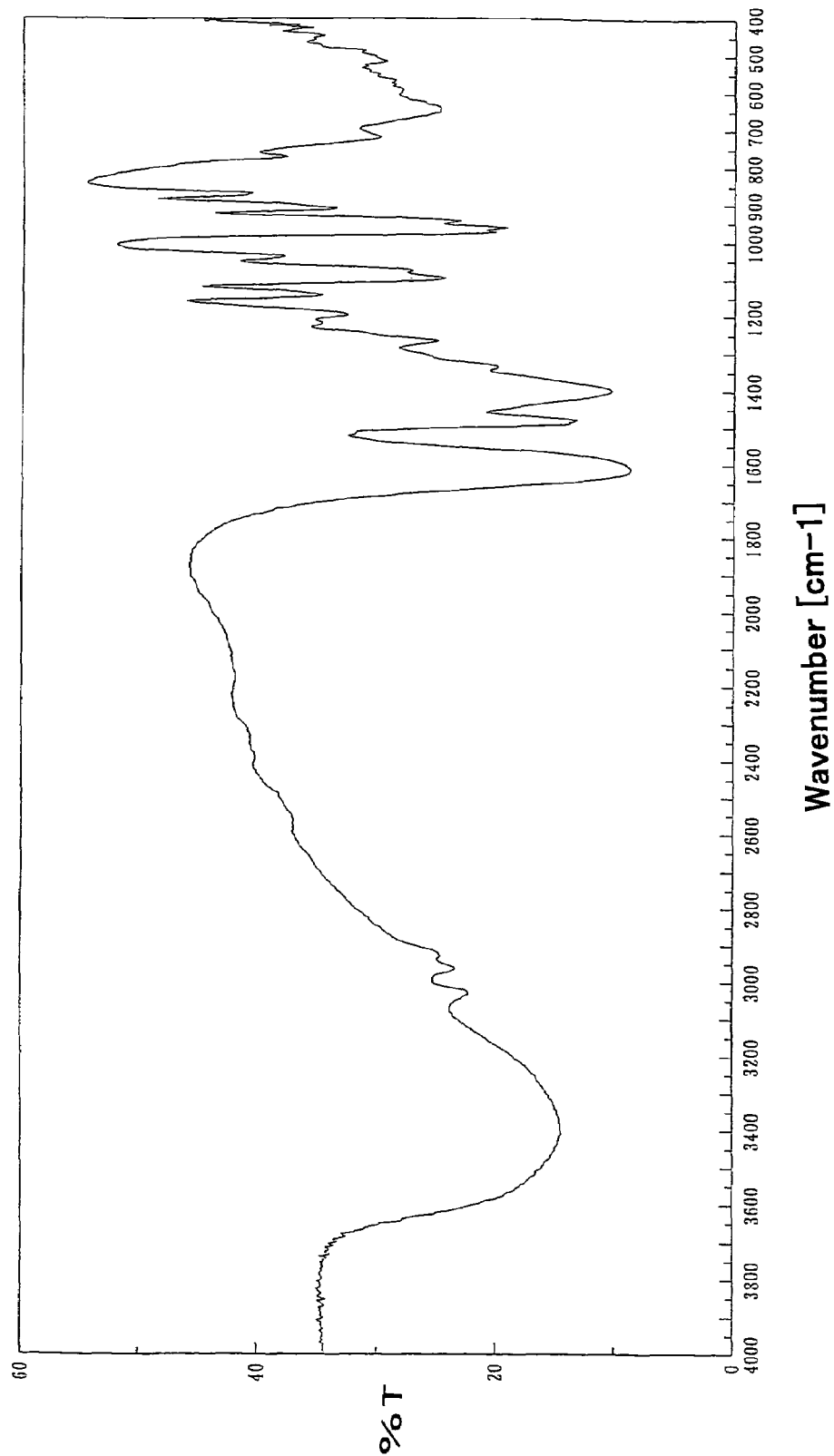
FIG. 5 shows a full chart of the IR absorption spectrum (IR) of L-carnitine/zinc(II) complex [Zn(Car)$_2$Cl$_2$] of the invention.

IR (KBr): full chart in FIG. 5.

Example 10

Production of bis(L-ascorbic acid)/zinc(II) complex [Zn(Vit-C)$_2$]

An aqueous solution of zinc(II) chloride (5 mmols) was added to an aqueous solution of L-ascorbic acid (10 mmols) and lithium hydroxide (10 mmols) with stirring. After left overnight, this was filtered, and the filtrate was concentrated. The insoluble substance was separated in ethanol through filtration, and the resulting filtrate was concentrated. The residue was processed with ether to obtain the intended product, powdery crystal.

Yield: 55%. m.p.: 158-198° C. (decomposed). [α]$_D$: −162.9° C. (H$_2$O).
Molecular formula: Zn(C$_6$H$_7$O$_6$).1.4H$_2$O,
Molecular weight: 440.9.
Elementary analysis:

| | |
|---|---|
| cald. (%) | C; 32.69, H; 3.84 |
| found (%) | C; 32.89, H; 4.12, |

Figure 6:
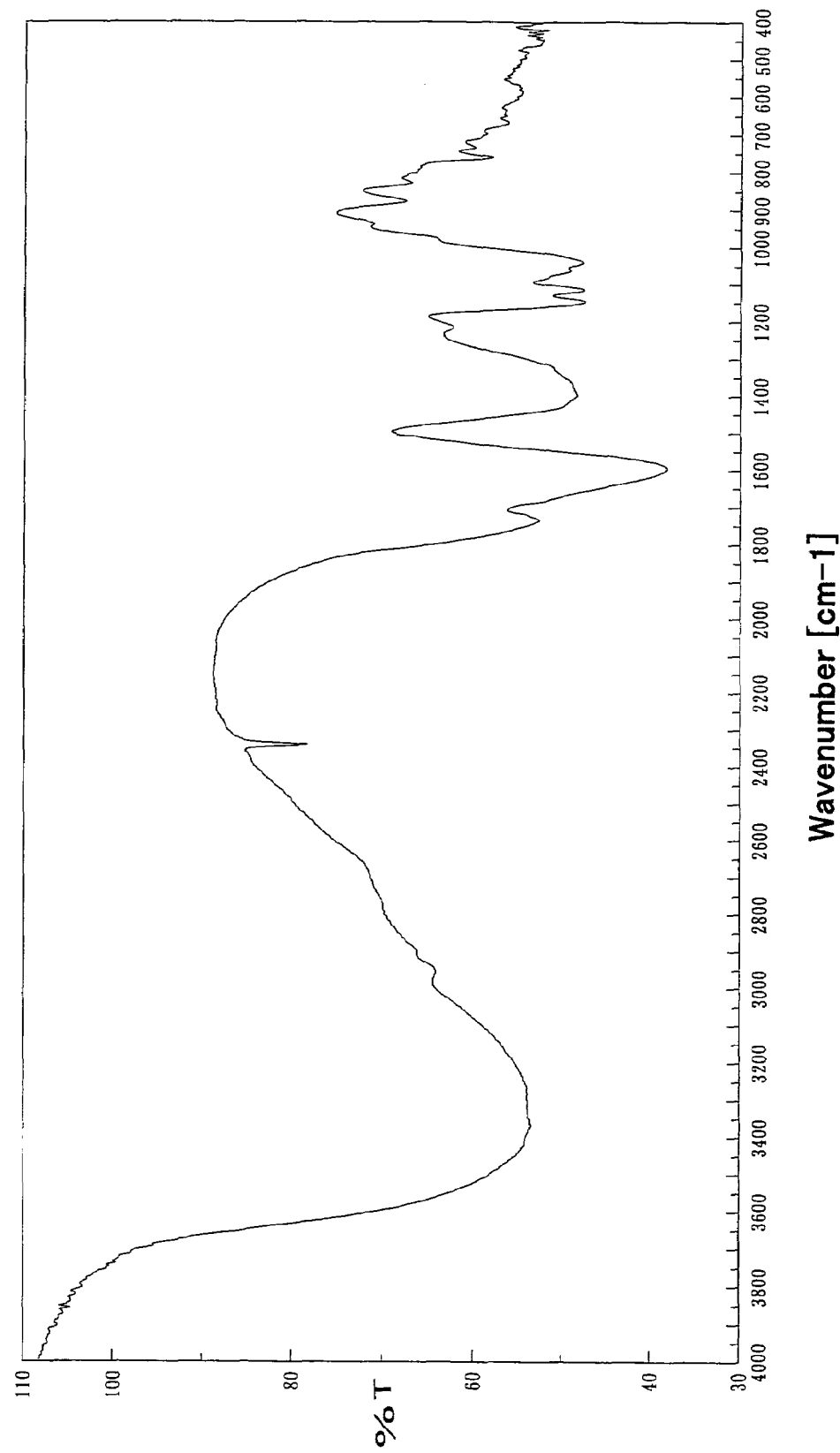
FIG. 6 shows a full chart of the IR absorption spectrum (IR) of bis(L-ascorbic acid)/zinc(II) complex [Zn(Vit-C)$_2$] of the invention.

IR (KBr): full chart in FIG. 6.

Example 11

Production of bis(vitamin U)/zinc(II) complex [Zn(Vit-U)Cl$_2$]

A methanol solution of zinc(II) chloride (10 mmols) was dropwise added to a methanol solution of vitamin U (10 mmols) and lithium hydroxide (10 mmols) with stirring. After this was left overnight, the precipitate formed was taken out through filtration, and the resulting white powdery crystal was washed three times with methanol to obtain the intended product.

Yield: 93%. m.p.: 117-120° C. [α]$_D$: −0.25° (H$_2$O).
Molecular formula: Zn(C$_6$H$_{13}$NO$_2$S)Cl$_2$/0.75H$_2$O,
Molecular weight: 313.0.
Elementary analysis:

| | |
|---|---|
| cald. (%) | C; 23.02, H; 4.67, N; 4.47 |
| found (%) | C; 22.93, H; 4.40, N; 4.54, |

Figure 7:
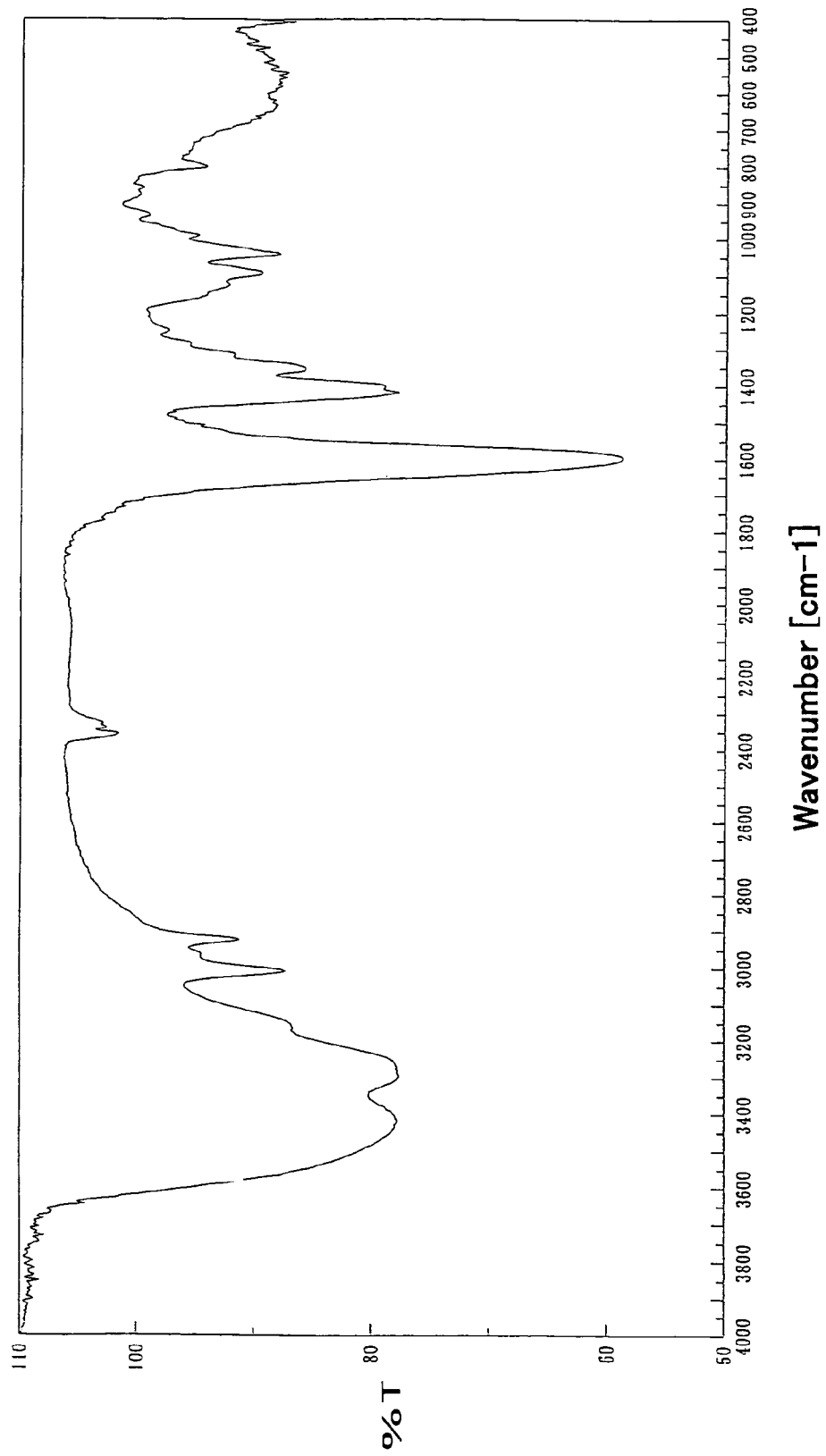
FIG. 7 shows a full chart of the IR absorption spectrum (IR) of bis(vitamin U)/zinc(II) complex [Zn(Vit-U)Cl$_2$] of the invention.

IR (KBr): full chart in FIG. 7.

Example 12

Production of bis(L-theanine)/zinc(II) complex [Zn(Tea)$_2$]

A methanol solution of zinc(II) nitrate.6H$_2$O (5 mmols) was dropwise added to a methanol solution of L-theanine (L-glutamine-monoethylamide) (10 mmols) and lithium hydroxide (10 mmols) with stirring. After this was left for 2 hours, the precipitate formed was taken out through filtration, and the resulting white powdery crystal was washed three times with methanol.

Yield: 99%. m.p.: >300° C. [α]$_D$: −6.4° (H$_2$O).
Molecular formula: Zn(C$_{14}$H$_{26}$N$_4$O$_6$),
Molecular weight: 411.8.
Elementary analysis:

| | |
|---|---|
| cald. (%) | C; 40.84, H; 6.36, N; 13.61 |
| found (%) | C; 40.89, H; 6.33, N; 13.46, |

Figure 8:
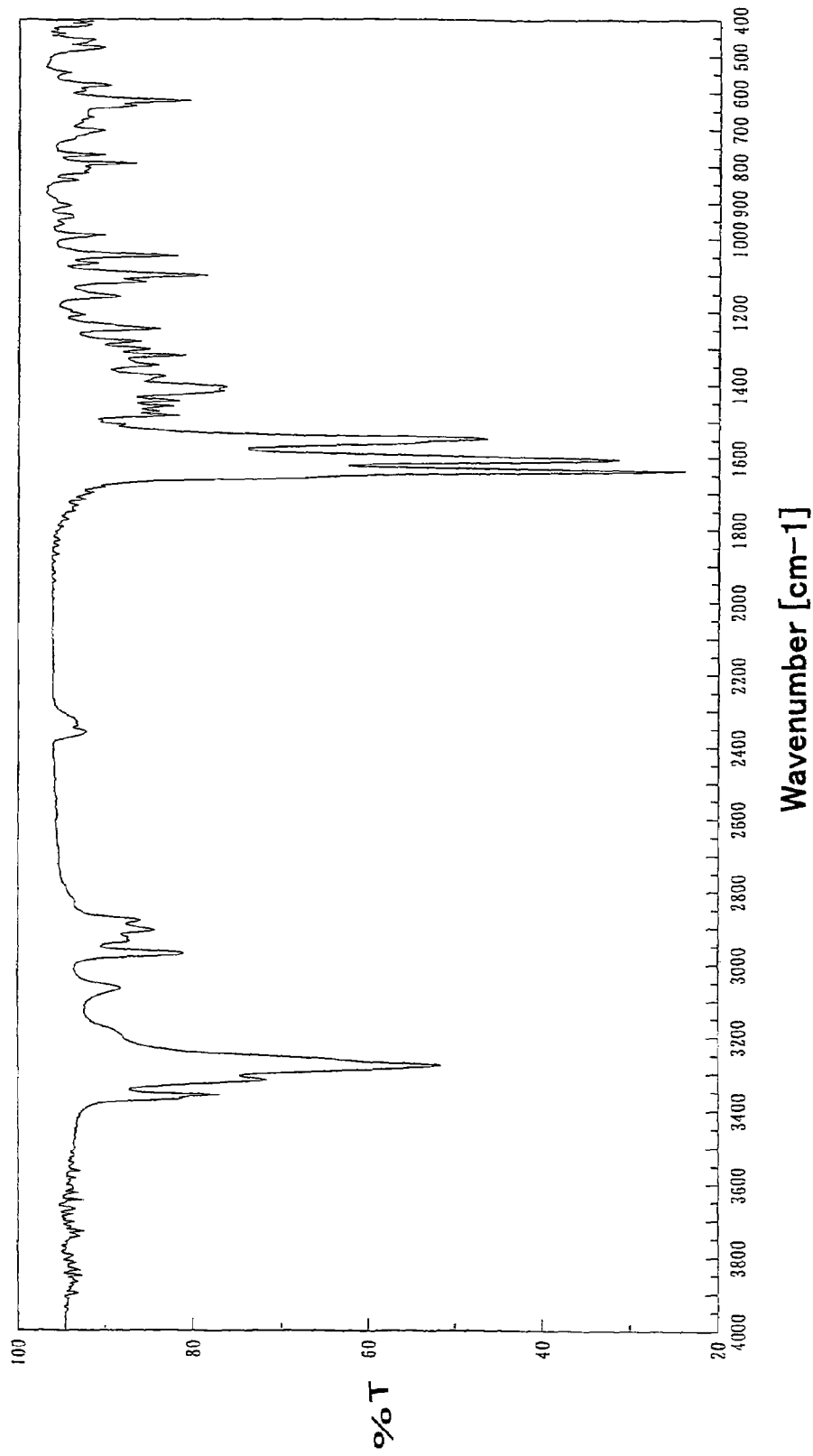
FIG. 8 shows a full chart of the IR absorption spectrum (IR) of bis(L-theanine)/zinc(II) complex [Zn(Tea)$_2$] of the invention.

IR (KBr): full chart in FIG. 8.

Pharmaceutical Test Example 1

According to the method described in *Biol. Pharm. Bull.*, 18, 719-725 (1995), the following experiment was carried out.

Isolation of Rat Fat Cells:

While anesthetized with ether, male Wistar rats (body weight, 200 g) were bled to death, and the fat cells were isolated from the fat tissue around the epididymis thereof, according to Rodbell's method (*J. Biol. Chem.*, 239, 375 (1964)). The fat cells were cut with scissors, and digested in a KRB buffer (glucose 10 mM, NaCl 120 mM, CaCl$_2$ 1.27 mM, MgSO$_4$ 1.2 mM, KCl 4.75 mM, KH$_2$PO$_4$ 1.2 mM and NaHCO 24 mM, pH=7.4) containing 20 mg/ml of bovine serum albumin (BSA) and 2 mg/ml of collagenase, at 37° C. for 1 hour. Filtered through a nylon mesh (250 mm), the fat cells were separated from the non-digested tissue, and then washed three times with the buffer mentioned above but not containing the collagenase to prepare a cell suspension of 2.5×10$^6$ cells/ml.

Effect of Zinc(II) Complex on Rat Fat Cells:

In silicon-processed vials, the fat cells isolated in the above (2.5×10$^6$ cells/ml) were pre-incubated in 1 ml of KRB buffer that contains a varying concentration (10$^{-4}$, 5×10$^{-4}$, 10$^{-3}$ M) of VOSO$_4$ different Zn(II) complexes of the invention and 20 mg/ml of BSA, at 37° C. for 0.5 hours. Next, 10$^{-5}$ M of epinephrine was added to the reaction mixture, and the resulting solution was incubated at 37° C. for 3 hours. The reaction was stopped by cooling the mixture with ice, and the mixture was centrifuged at 3000 rpm for 10 minutes. The free fatty acid (FFA) level in the extracellular solution was measured with an NEFA kit, and IC$_{50}$ of the test compound was calculated.

The results are given in FIG. 1, FIG. 2, FIG. 3 and Table 1 (mentioned above).

Pharmaceutical Test Example 2

<Test Method>

Type II diabetic model animals, KK-A$^y$ mice (8 weeks old), were used in the test. To those of a control group, administered was a 5% acacia solution (n=6). Any of Zn(2-AM-py)$_2$Cl$_2$, Zn(Lac)$_2$, Zn(Qui)$_2$, Zn(Car)$_2$Cl$_2$ and a mixed solution of zinc sulfate and vitamin U was dissolved in 5% acacia solution to prepare complex solutions. To those of a test group, administered was the complex solution (n=6). The dose was 2 mg Zn/kg to 3 mg Zn/kg. The acacia solution alone or the complex solution was intraperitoneally administered to each mouse once a day (but Zn(Car)$_2$Cl$_2$ was orally administered). The dose of the mixed solution of zinc sulfate and vitamin U was 3 mg Zn/kg for 3 days after the start of the administration, and on day 4 and thereafter, the dose was varied depending on the blood glucose level in each mouse (5 mg Zn/Kg to those having a blood glucose level of 200 mg/dl or more; and 3 mg Zn/kg to those having a blood glucose level of less than 200 mg/dl). This experiment was intraperitoneally administered to each mouse once a day.

To the mice of the control group, administered was 0.5 ml of the acacia solution alone.

The presence or absence of diabetes in the tested mice was confirmed by the average blood glucose level of at least 450 mg/dl and the average body weight of at least 35 g before administration.

The blood glucose level was measured with a simple blood glucose level meter (Glucocard, by Arclay Factory, Kyoto).

<Result>

Figure 9:
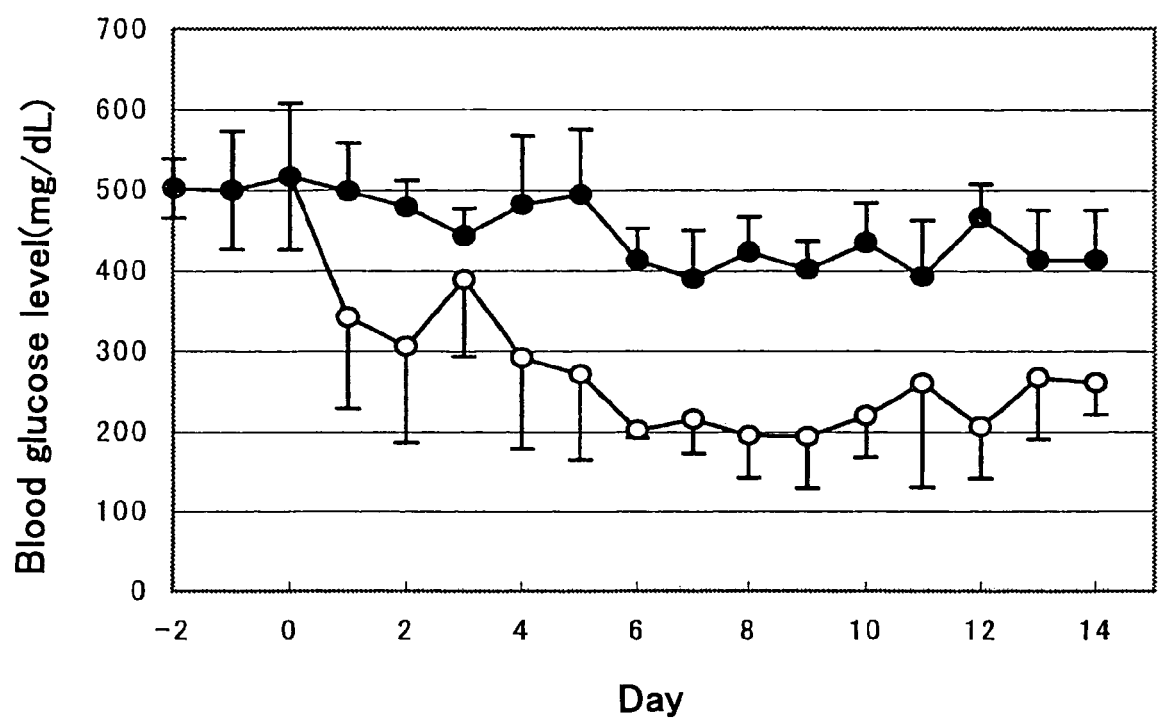
FIG. 9 shows the blood glucose level (BGL) change in KK-A$^y$ mice with intraperitoneal administration of Zn(2-AM-py)$_2$Cl$_2$ for 14 days (-o-) and with no administration thereof (control) (-•-).

FIG. 9 shows the blood glucose level (BGL) change in KK-A$^y$ mice with intraperitoneal administration of Zn(2-AM-py)$_2$Cl$_2$ for 14 days (-o-) and with no administration thereof (control) (-•-).

Figure 10:
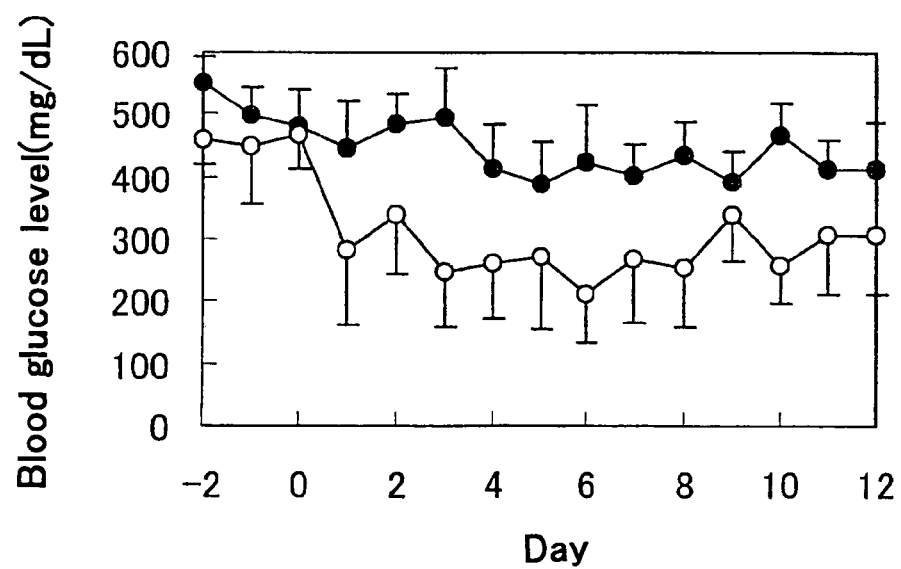
FIG. 10 shows the blood glucose level (BGL) change in KK-A$^y$ mice with intraperitoneal administration of Zn(Lac)$_2$ for 14 days (-o-) and with no administration thereof (control) (-•-).

FIG. 10 shows the blood glucose level (BGL) change in KK-A$^y$ mice with intraperitoneal administration of Zn(Lac)$_2$ for 14 days (-o-) and with no administration thereof (control) (-•-).

Figure 11:
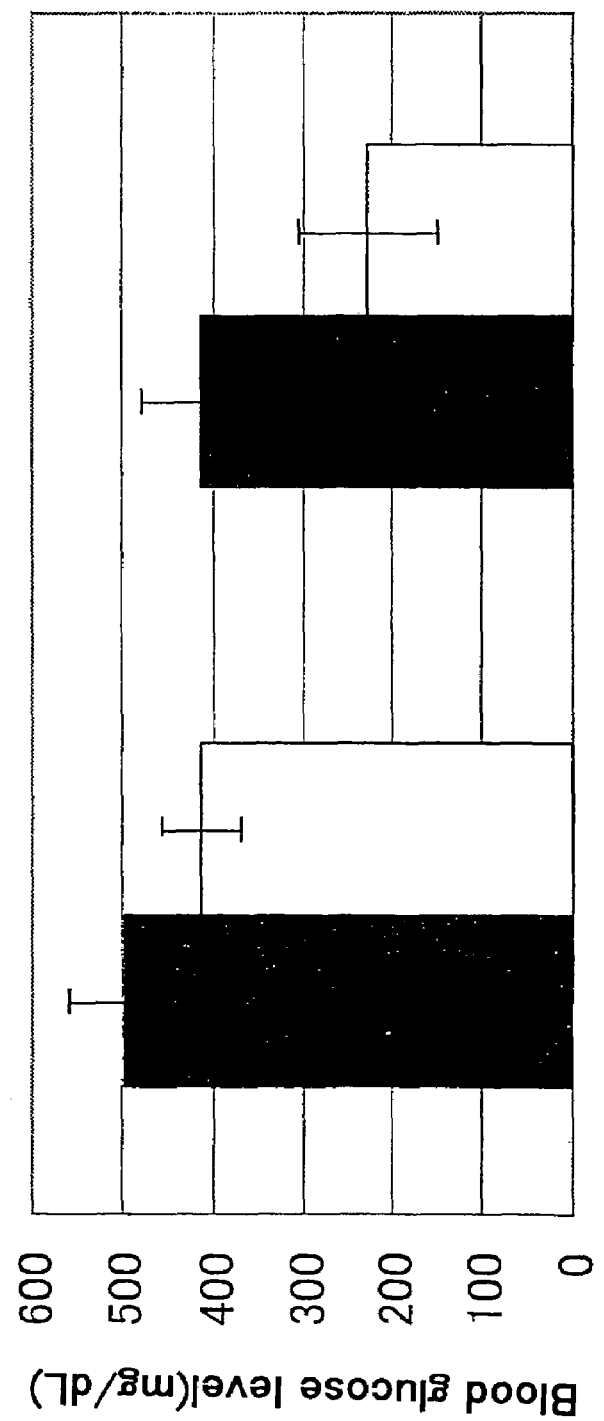
FIG. 11 shows the blood glucose level (BGL) change in KK-A$^y$ mice with intraperitoneal administration of Zn(Qui)$_2$ for 14 days (□) and with no administration thereof (control) (■).

FIG. 11 shows the blood glucose level (BGL) change in KK-A$^y$ mice with intraperitoneal administration of Zn(Qui)$_2$ for 14 days (□) and with no administration thereof (control) (■).

Figure 12:
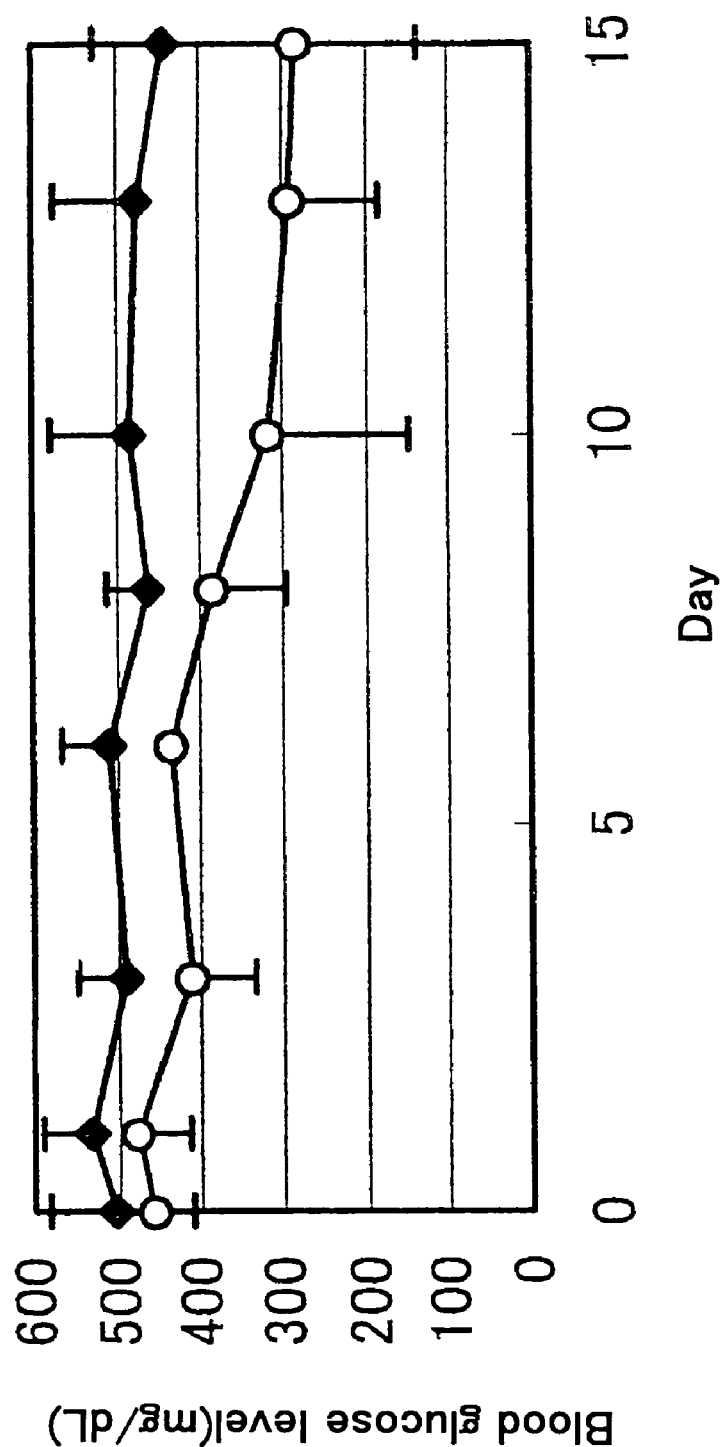
FIG. 12 shows the blood glucose level (BGL) change in KK-A$^y$ mice with oral administration of Zn(Car)$_2$Cl$_2$ for 14 days (-o-) and in those with oral administration of L-carnitine for 14 days (-♦-).

FIG. 12 shows the blood glucose level (BGL) change in KK-A$^y$ mice with oral administration of Zn(Car)$_2$Cl$_2$ for 14 days (-o-) and in those with oral administration of L-carnitine for 14 days (-♦-).

Figure 13:
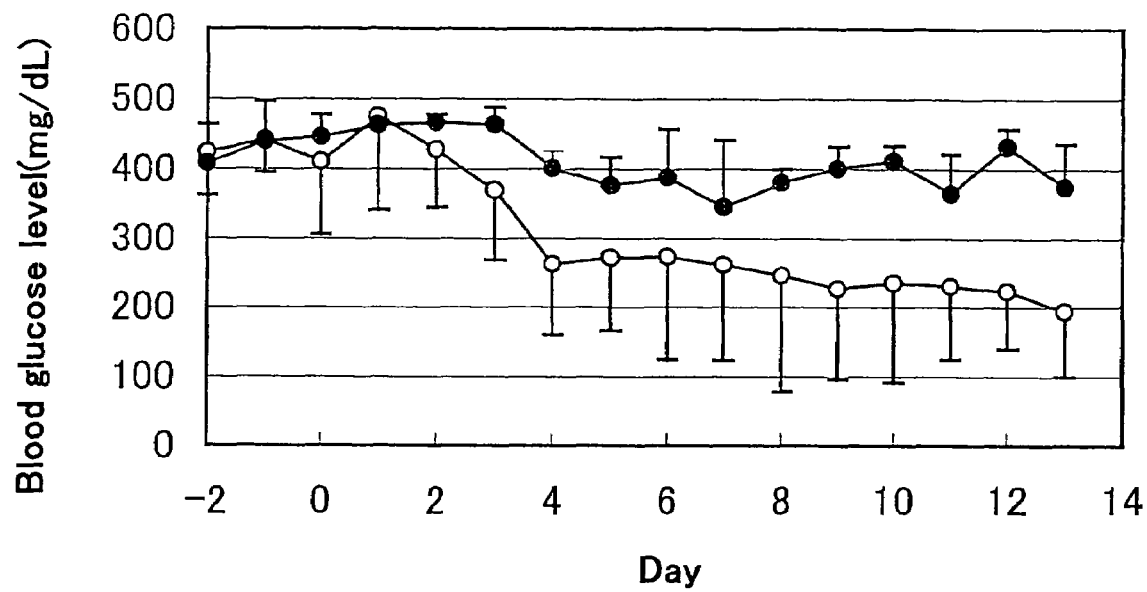
FIG. 13 shows the blood glucose level (BGL) change in KK-A$^y$ mice with intraperitoneal administration of a solution (about pH 7) prepared by mixing zinc sulfate and vitamin U in a molar ratio of 1:2 (that is, a solution of Zn(Vit-U)Cl$_2$)) for 14 days (-o-) and with no administration thereof (control) (-•-).

FIG. 13 shows the blood glucose level (BGL) change in KK-A$^y$ mice with intraperitoneal administration of a solution (about pH 7) prepared by mixing zinc sulfate and vitamin U in a molar ratio of 1:2 (that is, a solution of Zn(Vit-U)Cl$_2$)) for 14 days (-o-) and with no administration thereof (control) (-•-).

Figure 14:
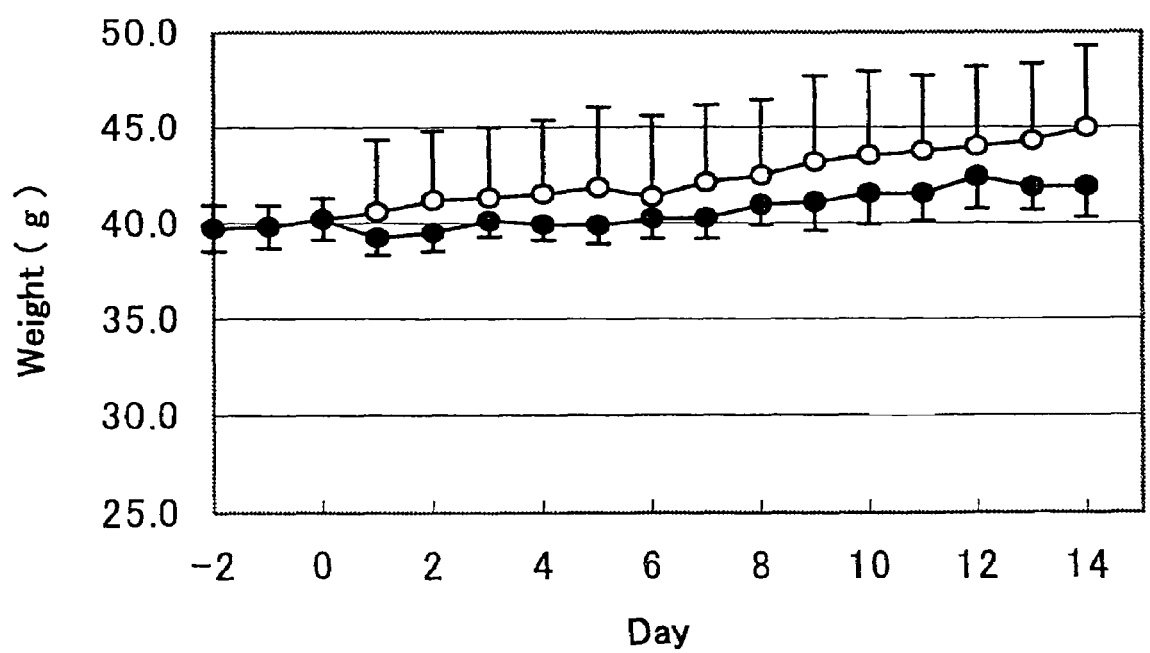
FIG. 14 shows the body weight change of KK-A$^y$ mice with intraperitoneal administration of Zn(2-AM-py)$_2$Cl$_2$ for 14 days (-o-) and with no administration thereof (control) (-•-).

FIG. 14 shows the body weight change of KK-A$^y$ mice with intraperitoneal administration of Zn(2-AM-py)$_2$Cl$_2$ for 14 days (-o-) and with no administration thereof (control) (-•-).

Figure 15:
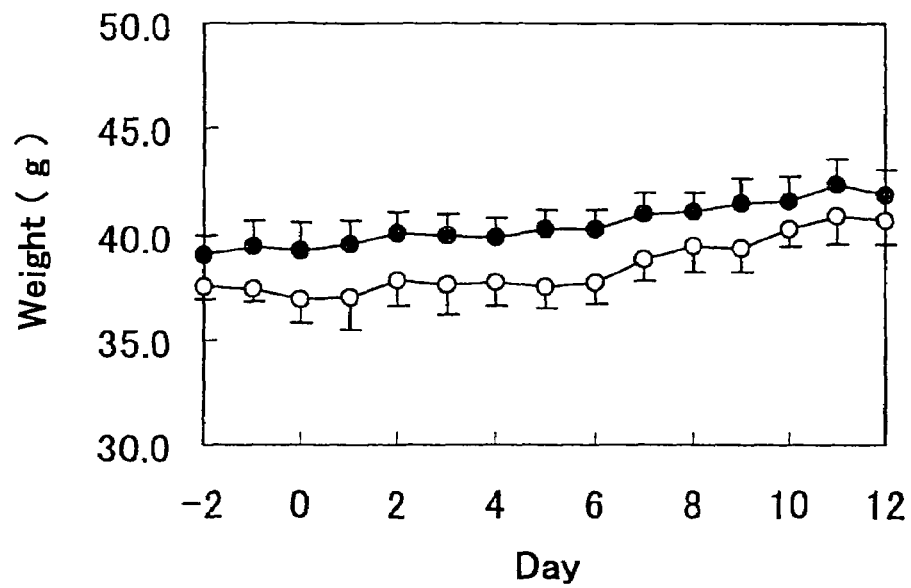
FIG. 15 shows the body weight change of KK-A$^y$ mice with intraperitoneal administration of Zn(Lac)$_2$ for 14 days (-o-) and with no administration thereof (control) (-•-).

FIG. 15 shows the body weight change of KK-A$^y$ mice with intraperitoneal administration of Zn(Lac)$_2$ for 14 days (-o-) and with no administration thereof (control) (-•-).

Figure 16:
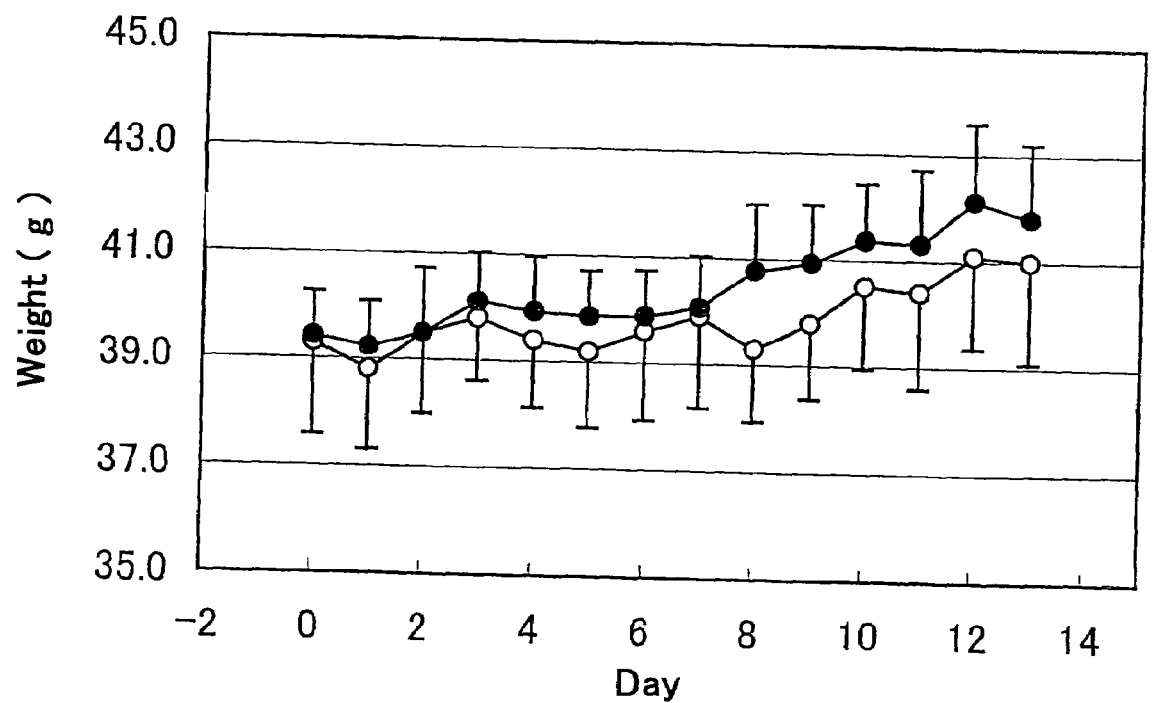
FIG. 16 shows the body weight change of KK-A$^y$ mice with intraperitoneal administration of Zn(Qui)$_2$ for 14 days (-o-) and with no administration thereof (control) (-•-).

FIG. 16 shows the body weight change of KK-A$^y$ mice with intraperitoneal administration of Zn(Qui)$_2$ for 14 days (-o-) and with no administration thereof (control) (-•-).

Figure 17:
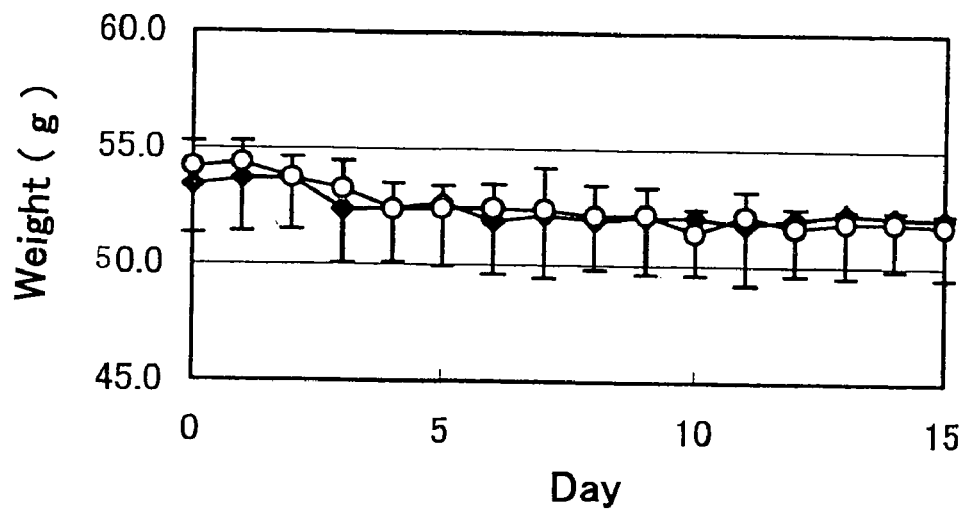
FIG. 17 shows the body weight change of KK-A$^y$ mice with oral administration of Zn(Car)$_2$Cl$_2$ for 14 days (-o-) and of those with oral administration of L-carnitine for 14 days (-♦-).

FIG. 17 shows the body weight change of KK-A$^y$ mice with oral administration of Zn(Car)$_2$Cl$_2$ for 14 days (-o-) and of those with oral administration of L-carnitine for 14 days (-♦-).

Figure 18:
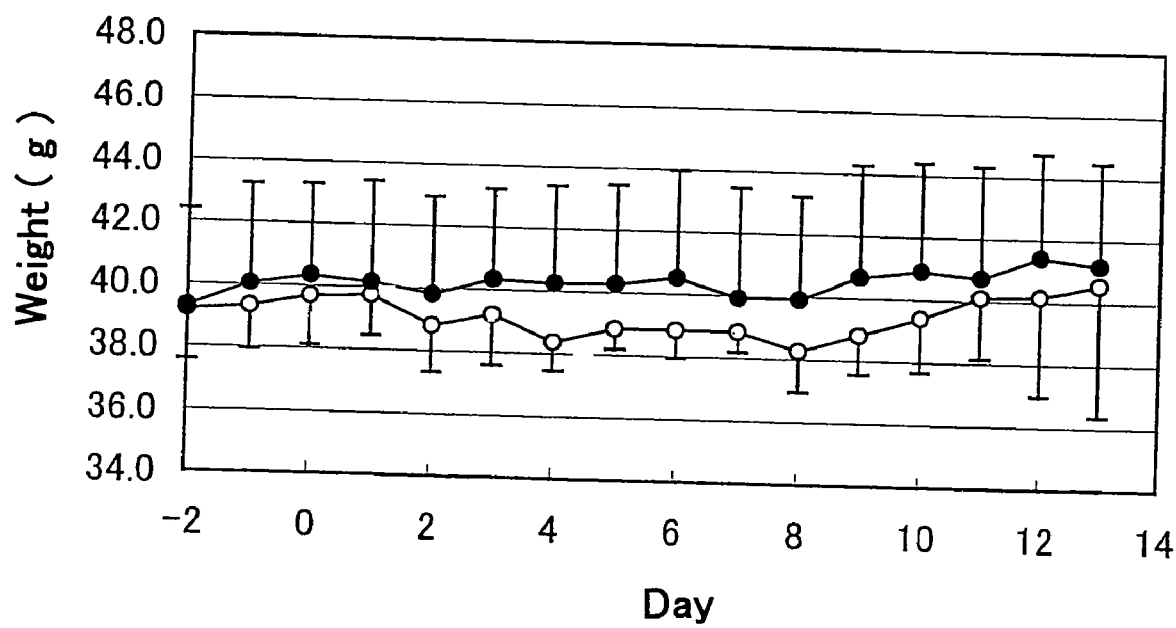
FIG. 18 shows the body weight change of KK-A$^y$ mice with intraperitoneal administration of a solution (about pH 7) prepared by mixing zinc sulfate and vitamin U in a molar ratio of 1:2 (that is, a solution of Zn(Vit-U)Cl$_2$)) for 14 days (-o-) and with no administration thereof (control) (-•-).

FIG. 18 shows the body weight change of KK-A$^y$ mice with intraperitoneal administration of a solution (about pH 7) prepared by mixing zinc sulfate and vitamin U in a molar ratio of 1:2 (that is, a solution of Zn(Vit-U)Cl$_2$)) for 14 days (-o-) and with no administration thereof (control) (-•-).

<Conclusion>

As is obvious from FIG. 9 to FIG. 13, the mice of the test groups, to which any of five different types of zinc(II) complexes of the invention had been administered, all enjoyed blood glucose level normalization as compared with those of the control groups.

Also obvious from FIG. 14 to FIG. 18, body weight reduction, one index of side effects was not almost seen in the mice of the test groups to which the zinc(II) complex of the invention had been administered.

Pharmaceutical Test Example 3

This is a glucose load test effected according to the method described in Biochem. Biophys. Res. Comm., 281, 1190-1193 (2001), in which the zinc(II) complex of the invention was intraperitoneally administered to KK-A$^y$ mice for 14 days or was not thereto. The mice were fed with nothing for 13 days, then 1 g/kg of glucose was orally administered to them, and the blood glucose level in them was measured at regular intervals.

<Result>

Figure 19:
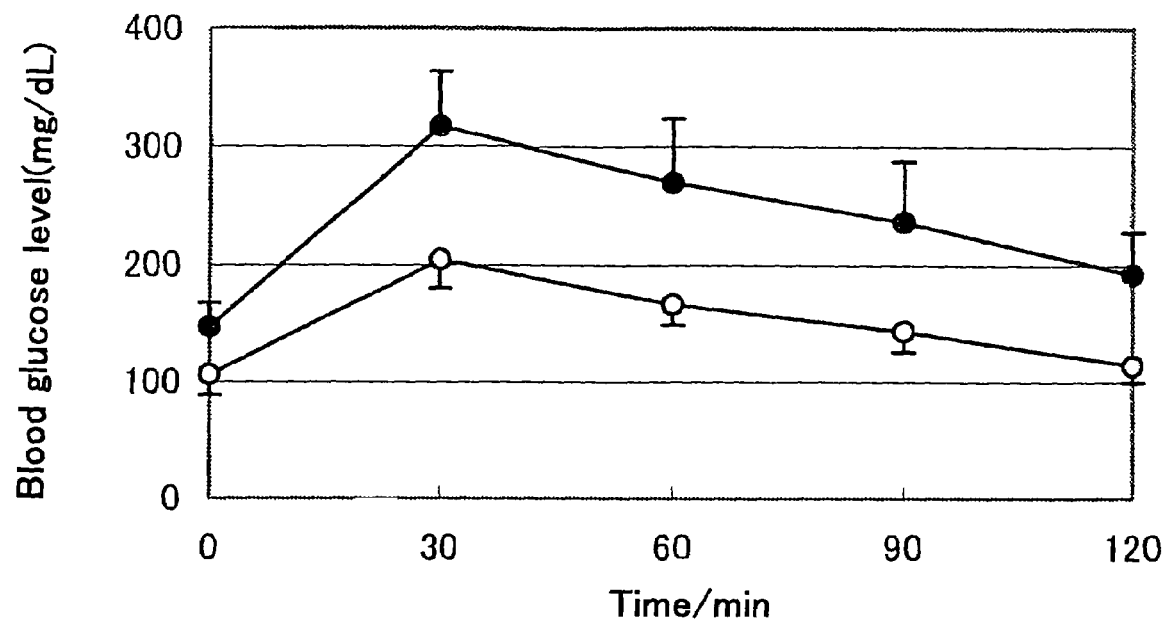
FIG. 19 shows the blood glucose curve observed in a glucose tolerance test in KK-A$^y$ mice with intraperitoneal administration of Zn(2-AM-py)$_2$Cl$_2$ for 14 days (-o-) and with no administration thereof (control) (-•-). The glucose tolerance test was effected after the 14 days administration.

FIG. 19 shows the blood glucose curve observed in a glucose tolerance test in KK-A$^y$ mice with intraperitoneal administration of Zn(2-AM-py)$_2$Cl$_2$ for 14 days (-o-) and with no administration thereof (control) (-•-). The glucose tolerance test was effected after the 14 days administration.

Figure 20:
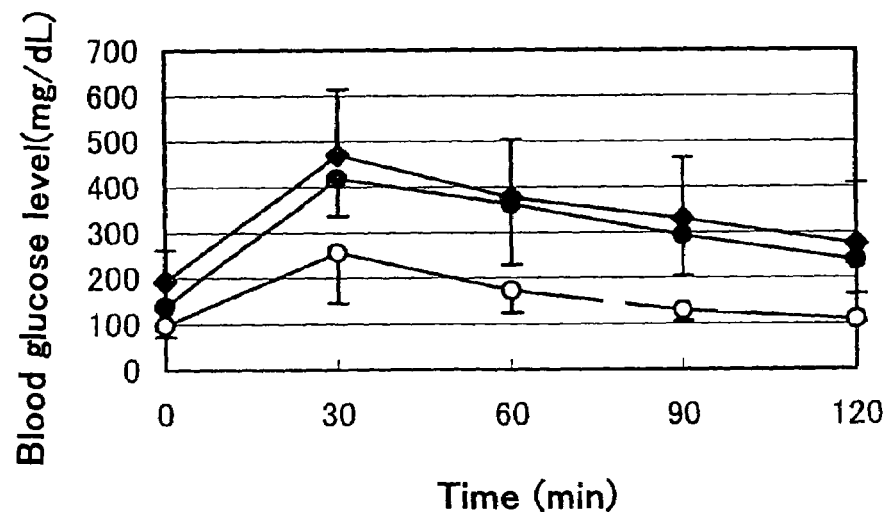
FIG. 20 shows the blood glucose curve observed in a glucose tolerance test in KK-A$^y$ mice with oral administration of Zn(Car)$_2$Cl$_2$ for 14 days (-o-), with oral administration of L-carnitine for 14 days (-♦-), and with administration of acacia solution alone for 14 days (control) (-•-). The glucose tolerance test was effected after the 14 days administration.

FIG. 20 shows the blood glucose curve observed in a glucose tolerance test in KK-A$^y$ mice with oral administration of Zn(Car)$_2$Cl$_2$ for 14 days (-o-), with oral administration of L-carnitine for 14 days (-♦-), and with administration of acacia solution alone for 14 days (control) (-•-). The glucose tolerance test was effected after the 14 days administration.

Figure 21:
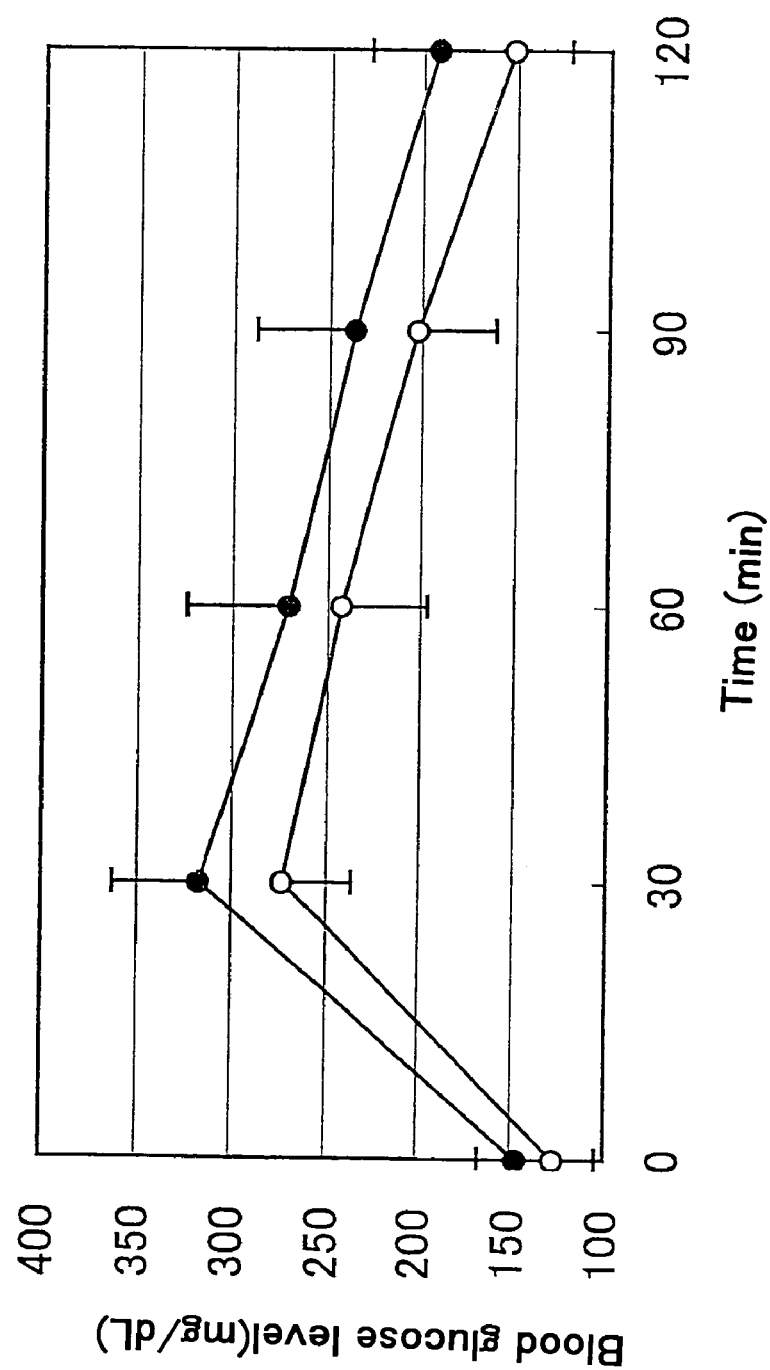
FIG. 21 shows the blood glucose curve observed in a glucose tolerance test in KK-A$^y$ mice with intraperitoneal administration of Zn(Qui)$_2$ for 14 days (-o-) and with no administration thereof (control) (-•-). The glucose tolerance test was effected after the 14 days administration.

FIG. 21 shows the blood glucose curve observed in a glucose tolerance test in KK-A$^y$ mice with intraperitoneal administration of Zn(Qui)$_2$ for 14 days (-o-) and with no administration thereof (control) (-•-). The glucose tolerance test was effected after the 14 days administration.

Figure 22:
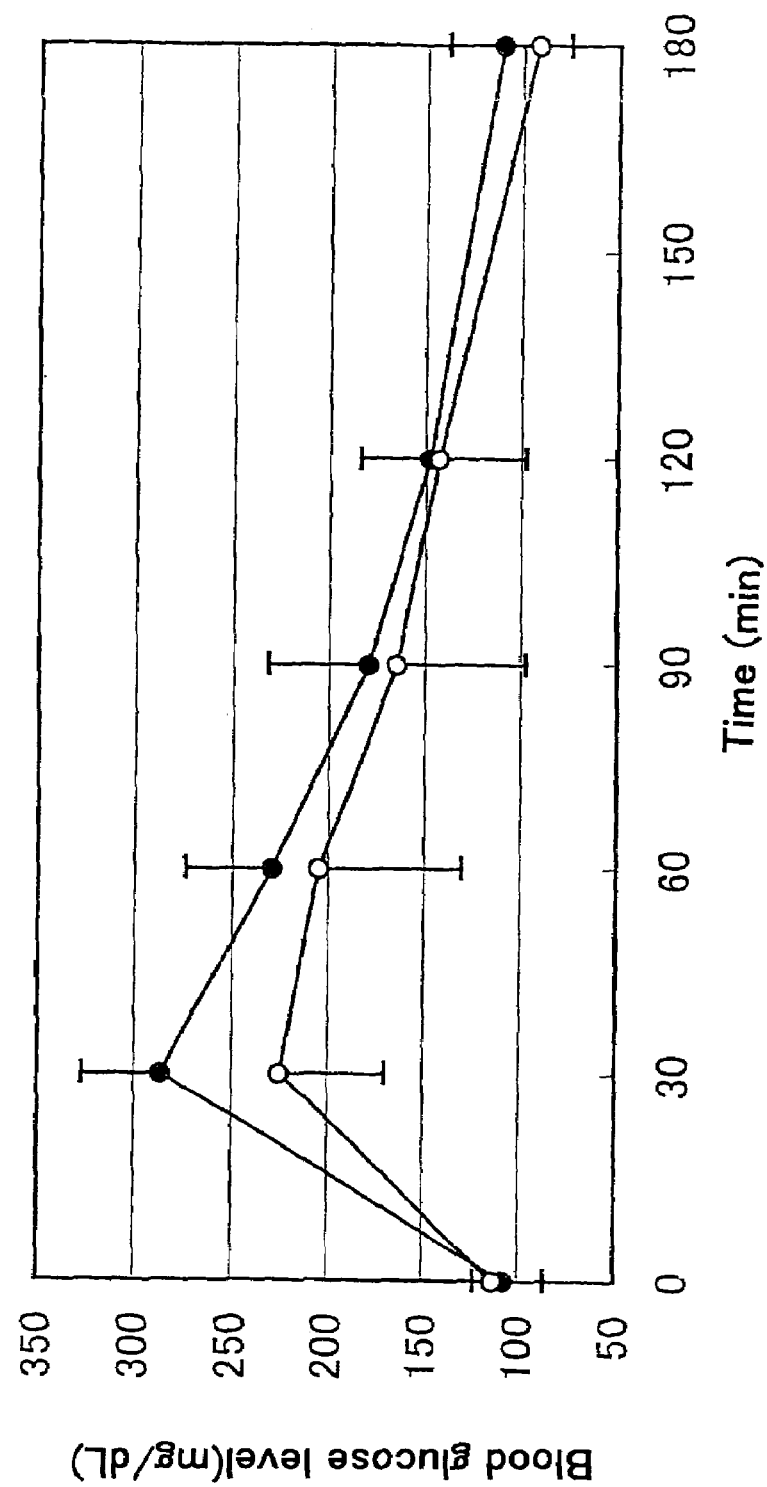
FIG. 22 shows the blood glucose curve observed in a glucose tolerance test in KK-A$^y$ mice with intraperitoneal administration of a solution (about pH 7) prepared by mixing zinc sulfate and vitamin U in a molar ratio of 1:2 (that is, a solution of Zn(Vit-U)Cl$_2$)) for 14 days (-o-) and with no administration thereof (control) (-•-). The glucose tolerance test was effected after the 14 days administration.

FIG. 22 shows the blood glucose curve observed in a glucose tolerance test in KK-A$^y$ mice with intraperitoneal administration of a solution (about pH 7) prepared by mixing zinc sulfate and vitamin U in a molar ratio of 1:2 (that is, a solution of Zn(Vit-U)Cl$_2$)) for 14 days (-o-) and with no administration thereof (control) (-•-). The glucose tolerance test was effected after the 14 days administration.

<Conclusion>

As is obvious from FIG. 19, the mice with 13-hour fasting after 14-day intraperitoneal administration of Zn(2-AM-py)$_2$Cl$_2$ had a low peak top of blood glucose level after glucose administration thereto, as compared with those with no complex administration. In the former, the blood glucose level smoothly lowered and after 120 minutes, it reached almost the normal level.

Also obvious from FIG. 20, the mice with 13-hour fasting after 14-day intraperitoneal administration of Zn(2-AM-py)$_2$Cl$_2$ had a low peak top of blood glucose level after glucose administration thereto, as compared with those with 13-hour fasting after 14-day oral administration of L-carnitine and those with 14-day administration of acacia solution alone. In the former, the blood glucose level smoothly lowered and after 120 minutes, it reached almost the normal level.

Further obvious from FIG. 21 and FIG. 22, the mice with 14-day intraperitoneal administration of Zn(Qui)$_2$ or Zn(Vit-U)Cl$_2$ followed by the glucose load test were significantly ameliorated in point of their diabetic condition than the diabetic mice (control mice), though their effect was somewhat lower than that of the mice administered with Zn(2-AM-py)$_2$Cl$_2$ or Zn(Car)$_2$Cl$_2$.

Example 13

30 g of water was mixed with 100 g of butter, 30 g of sugar, 200 g of wheat, 0.5 to 5 g of sodium bicarbonate and 3 g of Zn(Lac)$_2$. The resulting mixture was heated and baked into soft cookies.

Examples 14 to 18

Soft cookies were produced in the same manner as in Example 13, for which, however, 3 g of Zn(Qui)$_2$, Zn(Car)$_2$Cl$_2$, Zn(Vit-C)$_2$, Zn(Vit-U)Cl$_2$ or Zn(Tea)$_2$ was used in place of 3 g of Zn(Lac)$_2$ in Example 13.

Example 19

Soft cookies were produced in the same manner as in Example 13, for which, however, 1 to 5 g of Zn(Lac)$_2$ and 1 to 20 g of DHA-containing fish oil were used in place of 3 g of Zn(Lac)$_2$ in Example 13.

Example 20

Various juices were produced by mixing 1 to 50 g of Zn(Vit-C)$_2$, pH controlling agent (sodium hydroxide), sweetener and powdery juice stock.

INDUSTRIAL APPLICABILITY

The zinc(II) complex of the invention is highly stable and has fat-soluble insulin-like activity and hypotensive activity. Accordingly, the zinc(II) complex of the invention is extremely useful for medicines that are used for preventives/remedies for glucose tolerance disorders, diabetes (e.g., type II diabetes), insulin-resistant syndromes (e.g., insulin receptor disorders), polycystic ovary syndromes, hyperlipemia, atherosclerosis, cardiovascular disorders (e.g., stenocardia, cardiac insufficiency), hyperglycemia, hypertension, stenocardia, pulmonary hypertension, congestive cardiac insufficiency, diabetic complications (e.g., diabetic gangrene, diabetic arthropathy, diabetic glomerulosclerosis, diabetic skin disorders, diabetic neuropathy, diabetic cataract, diabetic retinopathy), taste disorders, skin disorders, etc. In addition, it is much expected for health (supplementary) foods and nutrient (supplementary) foods that are effective for prevention and remedy of insulin and blood glucose-related disorders.

The invention claimed is:

1. A method for lowering blood glucose level in a subject comprising administering to the subject a zinc(II) organic complex having, as a ligand, a compound of the formula (1) (when they are optically active compounds, they have both (R)-form and (S)-form thereof):

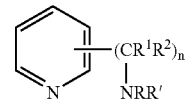

(1)

wherein R, R', R$^1$ and R$^2$ each independently represents a hydrogen atom, an alkyl group, an aryl group, or an aralkyl group; and n indicates an integer of from 1 to 3.

2. The method according to claim 1, wherein the zinc(II) organic complex is administered orally.

* * * * *